US006489349B1

(12) United States Patent
Bencherif et al.

(10) Patent No.: US 6,489,349 B1
(45) Date of Patent: Dec. 3, 2002

(54) PHARMACEUTICAL COMPOSITIONS FOR INHIBITION OF CYTOKINE PRODUCTION AND SECRETION

(75) Inventors: Merouane Bencherif; William Scott Caldwell, both of Winston-Salem; Gary Maurice Dull, Lewisville; Grayland Page Dobson, Winston-Salem, all of NC (US)

(73) Assignee: Targacept, Inc., Winston-Salem, NC (US)

(*) Notice: Subject to any disclaimer, the term of this patent is extended or adjusted under 35 U.S.C. 154(b) by 0 days.

(21) Appl. No.: 09/656,284

(22) Filed: Sep. 6, 2000

Related U.S. Application Data

(60) Division of application No. 09/295,181, filed on Apr. 20, 1999, now Pat. No. 6,166,048, and a continuation-in-part of application No. 08/631,761, filed on Apr. 23, 1996, now abandoned.

(51) Int. Cl.$^7$ .............................................. A61K 31/44
(52) U.S. Cl. ...................................................... 514/357
(58) Field of Search .......................................... 514/357

(56) References Cited

U.S. PATENT DOCUMENTS

| | | |
|---|---|---|
| 5,212,188 A | 5/1993 | Caldwell et al. |
| 5,583,140 A | 12/1996 | Bencherif et al. |
| 5,597,919 A | 1/1997 | Dull et al. |
| 5,604,231 A | 2/1997 | Smith et al. |
| 5,616,707 A | 4/1997 | Crooks et al. |
| 5,616,716 A | 4/1997 | Dull et al. |
| 5,663,356 A | 9/1997 | Ruecroft et al. |
| 5,811,442 A | 9/1998 | Bencherif et al. |
| 5,852,041 A | 12/1998 | Cosford et al. |
| 5,861,423 A | 1/1999 | Caldwell et al. |

FOREIGN PATENT DOCUMENTS

| | | |
|---|---|---|
| WO | WO 95/29892 | 11/1995 |
| WO | WO 97/40011 | 10/1997 |
| WO | WO 98/25619 | 6/1998 |
| WO | WO 98/47899 | 10/1998 |

OTHER PUBLICATIONS

Pullan et al. "Transdermal Nicotine for Active Ulcerative Colitis," The New England Journal of Medicine, vol. 330, No. 12, Mar. 24, 1994, pp. 811–815.
International Search Report, PCT/US00/10551, Dec. 20, 2000.
Van Dijk, Jeanette P.M. et al., European Journal of Pharmacology, 278, R11–R12 (1995).
Hanisch, Uwe–Karsten et al., The Journal of Neuroscience, vol. 13 (8), pp. 3368–3374 (1993).
Madretsma, Stanley et al., European Journal of Gastroenterology & Hepatology, vol. 8, No. 10, pp. 1017–1020 (1996).
Madretsma, G. S. et al., Immunopharmacology, 35, pp. 47–51 (1996).
Peacock, Mark E. et al., J. Periodontal, vol. 64, No. 7, pp. 658–665 (1993).
Sandborn, W. J. et al., Ailment Pharmacol Ther., 11, pp. 663–671 (1997).
Zijlstra, F. J. et al., Gut, 35, pp. 247–251 (1994).
Pullan, Robert D., Ann R. Coll. Surg. Engl., 78, pp. 85–91 (1996).
Silverstein, Marc D., M.D. et al., Mayo Clin. Proc., vol. 69, pp. 425–429 (1994).
Birtwistle, Jon, Postgrad Med. J., vol. 72, pp. 714–718 (1996).
Ebadi, M. et al., Neurochem. Int., vol. 30, Nos. 4/5, pp. 347–374 (1997).
Matthys, Patrick Ph.D. et al, Nutrition, vol. 13, pp. 763–770 (1997).
Jonakait, G. Miller, TINS, vol. 16, No. 10, pp. 419–423 (1993).
Wallace, John L. et al., Proc. Soc. Exp. Biol. Med., vol. 214, pp. 192–203 (1997).
Barnes, Peter J., Int. J. Biochem. Cell Ciol., vol. 29, No. 6, pp. 867–870 (1997).
Sartor, R. Balfour M.D., The American Journal of Gastroenterology, vol. 92, No. 12 (1997).

*Primary Examiner*—William R. A. Jarvis
(74) *Attorney, Agent, or Firm*—Womble Carlyle Sandridge & Rice, PLLC

(57) ABSTRACT

Pharmaceutical compositions incorporate compounds that affect cytokine production and/or secretion. Such compounds include aryl substituted olefinic amine compounds, pyridyloxylalkylamines and phenoxyalkylamines, and aryl substituted amine compounds, such as 3-aminophenyl amine compounds. Such pharmaceutical compositions can be used for treating a wide variety of conditions, diseases and disorders, and particularly those associated with dysfunction of cytokine production and/or secretion. Of particular interest are pharmaceutical compositions useful for preventing and treating conditions, diseases and disorders associated with undesirably high levels of cytokine production and/or secretion. Such pharmaceutical compositions are useful for treating the effects of inflammatory bowel disease, inflammation, arthritis, cachexia in neoplastics diseases or associated with AIDS, and autoimmune diseases.

43 Claims, No Drawings

PHARMACEUTICAL COMPOSITIONS FOR INHIBITION OF CYTOKINE PRODUCTION AND SECRETION

RELATED APPLICATIONS

This application is a divisional of U.S. application Ser. No. 09/295,181, filed Apr. 20, 1999, now U.S. Pat. No. 6,166,048, and is continuation-in-part of U.S. application Ser. No. 08/631,761, filed Apr. 23, 1996, now abandoned titled "Pharmaceutical Compositions for Prevention and Treatment of Central Nervous System Disorders," which application is herein incorporated by reference.

BACKGROUND OF THE INVENTION

The present invention relates to pharmaceutical compositions, and particularly pharmaceutical compositions incorporating compounds that affect cytokine production and/or secretion. The present invention also relates to methods for treating a wide variety of conditions, diseases and disorders, and particularly those associated with dysfunction of cytokine production and/or secretion. Of particular interest are pharmaceutical compositions useful for preventing and treating conditions, diseases and disorders associated with undesirably high levels of cytokine production and/or secretion.

Cytokines are polypeptides that affect cell function and modulate interactions between cells associated with immune, inflammatory or hematopoietic responses. Cytokines include monokines (which are generally produced and secreted by mononuclear cells, such as macrophages and monocytes) and lymphokines (which are generally produced and secreted by lymphocytes). Examples of cytokines include interleukin-1 (IL-1), interleukin-6 (IL-6), interleukin-8 (IL-8) and tumor necrosis factor (TNF, which includes TNF-alpha and TNF-beta). Cytokines have been recognized as having numerous functions, particularly with regards to immune system and inflammatory responses. See, Ebadi et al., *Neurochem. Int.*, 30(4–5): 347–374 (1997).

However, excessive or unregulated cytokine production and secretion has been implicated in mediating or exacerbating various diseases and disorders, particularly those associated with deficiencies in immunoregulation and physiological conditions (e.g., inflammation). See, for example, Tamaka, *Jap. J. Clin. Med.*, 56(1): 97–101 (1998); Dinarello, *J. Biol. Regul. Homeostat. Ag.*, 11(3): 91–103 (1997); Moldawer et al., *Sem. Oncol.*, 25(1): 73–81 (1998); Balkwill, *J. Viral Hepat.*, 4(2): 6–15 (1997); Martin et al., *Eur. Resp. J.*, 10(9): 2139–2146 (1997) and PCT WO 98/25619. For example, pro-inflammatory cytokines are produced by a variety of cell types, play major roles in the regulation of host immune responses, and have been implicated in diverse pathologies. Exemplary pro-inflammatory cytokines include interleukin species, prostaglandin species, colony stimulating factor and tumor necrosis factor.

Cytokines mediate a wide range of symptoms associated with trauma and infection, such as fever, anorexia, tissue wasting (cachexia), acute phase protein production and immunomodulation. In part, such symptoms result form a coordinated response, in which the immune system is activated and biochemical actions occur. Although the cytokine mediated response is an essential part of the response to trauma and infection, excessive production of cytokines, or production of cytokines in an inappropriate biological context, are associated with mortality and pathology in a wide range of diseases. Exemplary diseases and disorders associated with excessive or unregulated cytokine production and/or secretion include malaria, sepsis, rheumatoid arthritis, inflammatory bowel disease, cancer and AIDS. See, for example, Grimble et al., *Zeitschrift fur Ernahrungswissenschaft*, 37(1): 57–65 (1998). See also, Barnes, *Int. J. Biochem. Cell Biol.*, 29(6): 867–870 (1997).

Nicotine has been proposed to have a number of pharmacological effects. For a discussion of reported pharmacological effects of nicotine, see U.S. Pat. No. 5,663,356 to Ruecroft et al. at col. 1, line 39 through col. 2, line 8. In addition, various nicotinic compounds have been reported as being useful for treating a wide variety of conditions and disorders. See, for example, Williams et al. *DN&P* 7(4):205–227 (1994), Arneric et al., *CNS Drug Rev.* 1(1):1–26 (1995), Arneric et al., *Exp. Opin. Invest. Drugs* 5(1): 79–100 (1996), Bencherif et al., *JPET* 279:1413–1421 (1996), Lippiello et al., *JPET* 279:1422–1429 (1996), Damaj et al., *Neuroscience* (1997), Holladay et al., *J. Med. Chem* 40(28): 4169–4194 (1997), Bannon et al., *Science* 279: 77–80 (1998), PCT WO 94/08992, PCT WO 97/19059, and U.S. Pat. No. 5,278,176 to Lin, U.S. Pat. No. 5,583,140 to Bencherif et al., U.S. Pat. No. 5,597,919 to Dull et al., U.S. Pat. No. 5,616,716 to Dull et al., U.S. Pat. No. 5,811,442 to Bencherif et al. and U.S. Pat. No. 5,852,041 to Cosford et al., and U.S. patent application Ser. No. 09/054,130.

Nicotine has been proposed as a treatment for inflammatory bowel disease, such as ulcerative colitis. See, for example, Lashner et al., *Digestive Diseases and Sciences*, 35(7): 827–832 (1990); Pullan et al., *N. Engl. J. Med.*, 330: 811–815 (1994); and Sanborn et al., *Aliment Pharmacol. Ther.*, 11: 663–671 (1997). See, also, Silverstein et al., *Mayo Clin. Proc.*, 69: 425–429 (1994) and Birtwistle, *Postgrad. Med. J.*, 72: 714–718 (1996); as well as the results of studies reported by Zijistra et al., *Gut*, 35: 247–251 (1994) and Pullan, *Ann. R. Coll. Surg. Eng.*, 78: 85–91 (1996). In addition, administration of nicotinic compounds has been suggested as useful in the prevention and treatment of inflammatory bowel disease. See, for example, U.S. Pat. No. 5,604,231 to Smith et al.

The existence of interaction between nicotinic processes and the immune system has been proposed. See, for example, Lukas et al., *Intl. Rev. Neurobiol.*, Vol. 34, pp. 25–130 (1992) and Jonakait, *TINS*, Vol. 16 (10), pp. 419–423 (1993). The administration of nicotine has been shown to elicit inhibition of IL-2 production. See, for example, Denicoff et al., *Ann. Intern. Med.*, Vol.107, pp. 293–300 (1987); Plata-Salaman et al., *Neurosc. Biobeh. Res.*, Vol. 15, pp.185–215 (1991) and Hanish et al., *J. Neurosc.*, Vol. 13, pp. 3368–3374 (1993). Nicotine has been reported to exhibit effects upon cytokine production. Zhang et al., *Int. J. Immunopharmacol.*, 18(8–9): 467–478 (1996). For example, nicotine has been reported to have an effect upon human gingival fibroblast reproduction. Peacock et al., *J. Periodtol*, 64(7): 658–665 (1 993). It also has been reported that nicotine has an observed inhibitory effect upon prostaglandins in an inverse dose dependent manner (i.e., with greatest inhibition in relation to the lowest dose). Zijlstra et al., *Gut*, 35: 247–251 (1994). In addition, nicotine has been reported to have an inhibitory effect upon T-helper 2 (TH2) cell function as determined by inhibition of IL-10 production. Madretsma et al., *Eur. J. Gastroen Hepat.*, 8(10): 1017–1020 (1996). Furthermore, it has been reported that nicotine exhibits immunoregulatory effects through modulation of cytokine production, as evidenced by an observed inhibition of IL-2 and TNF-alpha. Madretsma et al., *Immunopharmacology*, 35: 47–51 (1996). See, also, Van Dijk et al., *European Journal of Pharmacology*, 278(1): R11–2 (1995).

It has been reported that it would be desirable to control the undesirable effects exhibited by inflammatory mediators, such as cytokines. Sartor, *Amer. J. Gastroent.,* 92(12): S5–S11 (1997); Wallace et al.,*Proc. Soc. Exp. Biol. Med.,* 214(3): 192–203 (1997) and Matthys et al., *Nutrition,* 13(9): 763–770 (1997).

Thus, it would be desirable to provide a pharmaceutical composition useful for the prevention and treatment of conditions, diseases or disorders where inhibition of the production and/or secretion of specific cytokines is desired. It would be highly beneficial to provide individuals suffering from certain conditions, diseases or disorders with interruption of the symptoms associated therewith by the administration of a pharmaceutical composition that has a beneficial effect upon the production and secretion of cytokines. It also would be highly beneficial that such pharmaceutical composition not provide any significant associated side effects attendant with interaction of that composition with cardiovascular sites (e.g., increased heart rate and blood pressure) or at skeletal muscle sites.

SUMMARY OF THE INVENTION

The present invention relates to a method for providing or treating a wide variety of conditions, diseases and disorders, and particularly those associated with dysfunction of cytokine production and/or secretion. In particular, the present invention relates to a method for providing prevention or treatment of conditions associated with an alteration in normal cytokine production and/or secretion (e.g., undesirably high levels of cytokine production and/or secretion). The method involves administering to a patient an effective amount of a compound of the present invention. Compounds of the present invention include aryl substituted olefinic amine compounds, pyridyloxyalkylamines and phenoxyalkylamines, and aryl substituted amine compounds, such as 3-aminophenyl amine compounds. The method also involves administering pro-drug derivatives of compounds of the present invention.

The present invention, in another aspect, relates to a non-pharmaceutical composition comprising an effective amount of a compound of the present invention. Such a pharmaceutical composition incorporates a compound which, when employed in effective amounts, has the capability of affecting dysfunction associated with cytokine production and/or secretion, and hence has the capability of acting as a therapeutic agent for the prevention or treatment of those conditions associated with abnormal cytokine production and/or secretion. Those compositions also can include pro-drug derivatives of compounds of the present invention.

The pharmaceutical compositions of the present invention are useful for the prevention or treatment of conditions associated with dysfunction of cytokine production and/or secretion. In particular, the pharmaceutical compositions are useful in inhibiting cytokine production and/or secretion. The pharmaceutical compositions provide therapeutic benefit to individuals suffering from such conditions and exhibiting clinical manifestations of such disorders in that the compounds within those compositions have the potential to (i) prevent and/or suppress the production and/or secretion of cytokines, and (ii) not provide appreciable adverse side effects (e.g., significant increases in blood pressure and heart rate, and significant effects upon skeletal muscle). The pharmaceutical compositions of the present invention are believed to be safe and effective with regards to prevention and treatment of conditions associated with dysfunction of cytokine production and/or secretion.

DETAILED DESCRIPTION OF THE PREFERRED EMBODIMENTS

The compounds useful in carrying out the present invention include compounds of the formula:

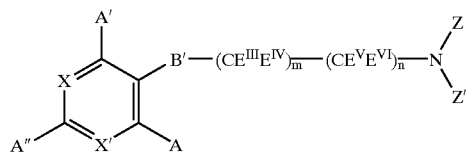

Each of X and X' are individually nitrogen or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., *Chem. Rev.* 91:165 (1991); m is an integer and n is an integer such that the sum of m plus n is 1, 2, 3, 4, 5, 6, 7, or 8, preferably is 1, 2, or 3, and most preferably is 2 or 3; and B' is oxygen, nitrogen-containing moiety (e.g., NR') or sulfur, or a substituted or unsubstituted two atom bridging species wherein at least one atom is carbon bonded to the aromatic ring of the structure and the other atom is carbon, oxygen, nitrogen or sulfur. As such, B', can be selected from any of the following:

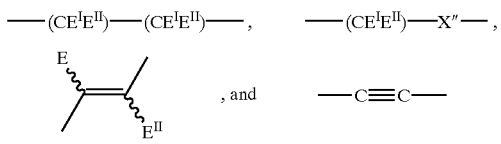

(e.g., alkyl-containing, olefinic or acetylinic linkage, unsubstituted or substituted moieties) with X" being oxygen, a nitrogen-containing moiety (e.g., NR') or sulfur, and the wavy lines in the structure indicating that the compound can have the cis (Z) or trans (E) form. $E^I$, $E^{II}$, $E^{III}$, $E^{IV}$, $E^V$ and $E^{VI}$ individually represent hydrogen or a suitable non-hydrogen substituent (e.g., alkyl, substituted alkyl, halo substituted alkyl, cycloalkyl, substituted cycloalkyl, heterocyclyl, substituted heterocyclyl, aryl, substituted aryl, alkylaryl, substituted alkylaryl, arylalkyl or substituted arylalkyl), preferably lower alkyl (e.g., straight chain or branched alkyl including $C_1$–$C_8$, preferably $C_1$–$C_5$, such as methyl, ethyl, or isopropyl) or halo substituted lower alkyl (e.g., straight chain or branched alkyl including $C_1$–$C_8$, preferably $C_1$–$C_5$, such as trifluoromethyl or trichloromethyl), cycloalkyl, substituted cycloalkyl, heterocyclyl, substituted heterocyclyl, aryl, substituted aryl, alkylaryl, substituted alkylaryl, arylalkyl or substituted arylalkyl. Generally all of $E^I$, $E^{II}$, $E^{III}$, $E^{IV}$, $E^V$ and $E^{VI}$ are hydrogen, or at least one of $E^I$, $E^{II}$, $E^{III}$, $E^{IV}$, $E^V$ and $E^{VI}$ is non-hydrogen and the remaining $E^I$, $E^{II}$, $E^{III}$, $E^{IV}$, $E^V$ and $E^{VI}$ are hydrogen. In addition, $E^{III}$ and $E^{IV}$ or $E^V$ and $E^{VI}$ and their associated carbon atom can combine to form a ring structure such as cyclopentyl, cyclohexyl or cycloheptyl; or $E^{III}$ and $E^V$ (when located on immediately adjacent carbon atoms) and their associated carbon atoms can combine to form a ring structure such as cyclopentyl, cyclohexyl or cycloheptyl. Z and $Z^I$ individually represent hydrogen, alkyl (e.g., straight chain or branched alkyl including $C_1$–$C_8$, preferably $C_1$–$C_5$, such as methyl, ethyl, or isopropyl), substituted alkyl, acyl, alkoxycarbonyl, or aryloxycarbonyl; and preferably at least one of Z and $Z^I$ is hydrogen or both of Z and $Z^I$ are hydrogen, and most preferably Z is hydrogen and $Z^I$ is methyl. Alternatively, Z is hydrogen and $Z^I$ represents a ring structure (cycloalkyl, heterocyclyl or aryl), such as cyclopropyl, cyclobutyl, cyclopentyl, cyclohexyl, cycloheptyl, adamantyl, quinuclidinyl, pyridinyl, quinolinyl, pyrimidinyl, phenyl, benzyl, thiazolyl or oxazolyl (where any of the foregoing can be suitably substituted with at least one substituent group, such as alkyl, alkoxyl, halo, or amino substituents); alternatively Z is hydrogen and $Z^I$ is propargyl; alternatively Z, $Z^I$, and the associated nitrogen atom can form a ring structure such as aziridinyl, azetidinyl, pyrrolidinyl, piperidinyl, morpholinyl, 2-imino-2,3-dihydrothiazolyl or 2-imino-2,3-dihydrooxazolyl, and in certain situations, piperazinyl (e.g., piperazine); $Z^I$ and $E^V$ (when n is 1) and the associated carbon and nitrogen atoms can combine to form a monocyclic ring structure such as azetidinyl, pyrrolidinyl, piperidinyl, piperazinyl, or a bicyclic ring structure such as 3-(2-azabicyclo[4.2.0]octyl), 3-(2-azabicyclo[2.2.2]octyl), or 3-(2-azabicyclo[2.2.1]heptyl); however it is preferred that when $Z^I$ and $E^V$ and the associated carbon and nitrogen atoms combine to form such a ring, neither $E^{VI}$ nor $E^{III}$ are substituted or unsubstituted aryl, heteroaryl, benzhydryl or benzyl; $Z^I$ and $E^{III}$ (when n is 1) and the associated carbon and nitrogen atoms can combine to form a monocyclic ring structure such as azetidinyl, pyrrolidinyl, piperidinyl, or piperazinyl or a bicyclic ring structure such as 3-(2-azabicyclo[4.2.0]octyl), 3-(2-azabicyclo[2.2.2]octyl), or 3-(2-azabicyclo[2.2.1] heptyl); Z, $Z^I$ and $E^V$ (when n is 1) and the associated carbon and nitrogen atoms can combine to form a bicyclic ring structure such as quinuclidinyl, 2-(1-azabicyclo[2.2.1]-heptyl), or 2-(1-azabicyclo[3.3.0]octyl), or a tricyclic ring structure such as azaadamantyl; $Z^I$, $E^V$ and $E^{VI}$ (when n is 1) and the associated carbon and nitrogen atoms can combine to form a bicyclic ring structure such as 1-(2-azabicyclo[2.2.1]heptyl); and Z, $Z^I$, $E^V$ and $E^{VI}$ (when n is 1) and the associated carbon and nitrogen atoms can combine to form a tricyclic ring structure. When X and X' represent a carbon atom bonded to a substituent species, that substituent species often has a sigma m value which is between about –0.3 and about 0.75, and frequently between about –0.25 and about 0.6. In certain circumstances the substituent species is characterized as having a sigma m value not equal to 0. For certain compounds, X is nitrogen; for other compounds X' is nitrogen; and for other compounds X and X' both are nitrogen. A, A' and A" individually represent those species described as substituent species to the aromatic carbon atom previously described for X and X'; and usually include hydrogen, halo (e.g., F, Cl, Br, or I), alkyl (e.g., lower straight chain or branched $C_{1-8}$ alkyl, but preferably methyl or ethyl), or $NX^{III} X^{IV}$ where $X^{III}$ and $X^{IV}$ are individually hydrogen or lower alkyl, including $C_1$–$C_8$, preferably $C_1$–$C_5$ alkyl. In addition, it is highly preferred that A is hydrogen, it is preferred that A' is hydrogen, and normally A" is hydrogen. Generally, both A and A' are hydrogen; sometimes A and A' are hydrogen, and A" is amino, methyl or ethyl; and often A, A' and A" are all hydrogen. Adjacent substituents of A, A' or A" (when X or X' are carbon bonded to a substituent component) can combine to form one or more saturated or unsaturated, substituted or unsubstituted carbocyclic or heterocyclic rings containing, but not limited to, ether, acetal, ketal, amine, ketone, lactone, lactam, carbamate, or urea functionalities. In a preferred embodiment, m is 1 or 2, n is 1, $E^I$, $E^{II}$, $E^{III}$, $E^{IV}$ and $E^{VI}$ each are hydrogen, and $E^V$ is hydrogen or alkyl (e.g., methyl). Depending upon the identity and positioning of each individual $E^I$, $E^{II}$, $E^{III}$, $E^{IV}$, $E^V$ and $E^{VI}$, certain compounds can be optically active. Additionally, compounds of the present invention can have chiral centers within the alkenyl side chain e.g., the compound can have an R or S configuration depending on the selection of $E^{III}$, $E^{IV}$, $E^V$ and $E^{VI}$, with the S configuration being preferred. Depending upon $E^I$, $E^{II}$, $E^{III}$, $E^{IV}$, $E^V$ and $E^{VI}$, compounds of the present invention have chiral centers, and the present invention relates to racemic mixtures of such compounds as well as enantiomeric compounds. Typically, the selection of m, n, $E^I$, $E^{II}$, $E^{III}$, $E^{IV}$, $E^V$ and $E^{VI}$ is such that up to about 4, and frequently up to 3, and usually 0, 1 or 2, of the substituents designated as $E^I$, $E^{II}$, $E^{III}$, $E^{IV}$, $E^V$ and $E^{VI}$ are non-hydrogen substituents (i.e., substituents such as lower alkyl or halo-substituted lower alkyl). Typically, X is CH, CBr or COR. Most preferably, X' is nitrogen. However, certain other preferred compounds are such that X' is C—NR'R", C—OR' or C—$NO_2$, more preferably C—$NH_2$, C—$NHCH_2$ or C—$N(CH_3)_2$, with $NH_2$ being most preferred. In addition, when X is carbon bonded to a substituent species, it is preferred that the substituent species is H, Br or OR', where R' preferably is methyl, ethyl, isopropyl, isobutyl or tertiary butyl. Depending upon the identity of B', it is possible that B', $A^I$ and the associated carbon atoms can combine to form a ring structure (e.g., a 5 or 6 membered ring); and B' and $E^{III}$ and the intervening atoms can combine to form a ring structure (e.g., cycloalkyl, substituted cycloalkyl, heterocyclyl, substituted heterocyclyl). More specifically, A, $A^I$, $A^{II}$ and the substituents of either X or X' (when each respective X and X' is carbon) include H, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", $CF_3$, OH, CN, $NO_2$, $C_2R'$, SH, $SCH_3$, $N_3$, $SO_2CH_3$, OR', $(CR'R")_qOR'$, O—$(CR'R")_qC_2R'$, SR', C(=O)NR'R", NR'C(=O)R", C(=O)R', $(CR'R")_qC_2R'$, C(=O)OR', OC(=O)R', OC(=O)NR'R" and NR'C(=O)OR" where q is an integer from 1 to 6 and R' and R" are individually hydrogen or alkyl (e.g., $C_1$–$C_{10}$ alkyl, preferably $C_1$–$C_5$ alkyl, and more preferably methyl, ethyl, isopropyl or isobutyl), cycloalkyl (e.g., cyclopropyl cyclobutyl, cyclopentyl, cyclohexyl, cycloheptyl, and adamantyl), a non-aromatic heterocyclic ring wherein the heteroatom of the heterocyclic moiety is separated from any other nitrogen, oxygen or sulfur atom by at least two carbon atoms (e.g., quinuclidinyl, pyrrolidinyl, and piperidinyl), an aromatic group-containing species (e.g., pyridyl, quinolinyl, pyrimidinyl, furanyl, phenyl, and benzyl where any of the foregoing can be suitably substituted with at least one substituent group, such as alkyl, alkoxyl, halo, or amino substituents). Other representative aromatic ring systems are set forth in Gibson et al., *J. Med. Chem.* 39:4065 (1996).

As employed herein, "alkyl" refers to straight chain or branched alkyl radicals including $C_1$–$C_8$, preferably $C_1$–$C_5$, such as methyl, ethyl, or isopropyl; "substituted alkyl" refers to alkyl radicals further bearing one or more substituent groups such as hydroxy, alkoxy, mercapto, aryl, heterocyclo, halo, amino, carboxyl, carbamyl, cyano, and the like; "alkenyl" refers to straight chain or branched hydrocarbon radicals including $C_1$–$C_8$, preferably $C_1$–$C_5$ and having at least one carbon-carbon double bond; "substituted alkenyl" refers to alkenyl radicals further bearing one or more substituent groups as defined above; "cycloalkyl" refers to saturated or unsaturated cyclic ring-containing radicals containing three to eight carbon atoms, preferably three to six carbon atoms; "substituted cycloalkyl" refers to cycloalkyl radicals further bearing one or more substituent groups as defined above; "aryl" refers to aromatic radicals having six to ten carbon atoms; "substituted aryl" refers to aryl radicals further bearing one or more substituent groups as defined above; "alkylaryl" refers to alkyl-substituted aryl radicals; "substituted alkylaryl" refers to alkylaryl radicals further bearing one or more substituent groups as defined above; "arylalkyl" refers to aryl-substituted alkyl radicals; "substituted arylalkyl" refers to arylalkyl radicals further bearing one or more substituent groups as defined above; "heterocyclyl" refers to saturated or unsaturated cyclic radicals containing one or more heteroatoms (e.g., O, N, S) as part of the ring structure and having two to seven carbon atoms in the ring; "substituted heterocyclyl" refers to heterocyclyl radicals further bearing one or more substituent groups as defined above; "acyl" refers to straight chain or branched alkyl- or substituted alkyl-carbonyl radicals including $C_1$–$C_8$, preferably $C_1$–$C_5$, such as formyl, acetyl, or propanoyl; "alkoxycarbonyl" refers to an alkyl or substituted alkyl radical attached to an O-carbonyl moiety; and "aryloxycarbonyl" refers to an aryl or substituted aryl radical attached to an O-carbonyl moiety.

Of particular interest are compounds of the formulae:

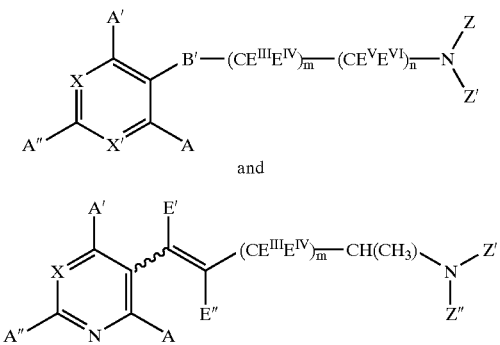

where m, n, $E^I$, $E^{II}$, $E^{III}$, $E^{IV}$, X, X', Z', Z", A, A' and A" are as defined hereinbefore, and the wavy line in the structures indicates that the compound can have a cis(Z) or trans(Z) form. Such compounds preferably have a trans(Z) form.

Representative compounds of the present invention are (3E) and (3Z)-N-methyl-4-(3-pyridyl)-2-methyl-3-buten-1-amine, (3E) and (3Z)-N-methyl-4-(3-pyridyl)-3-methyl-3-buten-1-amine, (5E) and (5Z)-N-methyl-6-(3-pyridyl)-5-hexen-3-amine, (4E) and (4Z)-N-methyl-5-(3-pyridyl)-2-methyl-4-penten-2-amine, (4E) and (4Z)-N-methyl-5-(3-pyridyl)-3-methyl-4-penten-2-amine, (4E) and (4Z)-N-methyl-5-(3-pyridyl)-4-penten-2-amine, (4E) and (4Z)-N-methyl-5-(3-pyridyl)-1,1,1-trifluoro-4-penten-2-amine, (4E) and (4Z)-N-methyl-5-(3-pyridyl)-4-methyl-4-penten-1-amine, (4E) and (4Z)-N-methyl-5-(3-pyridyl)-4-methyl-4-penten-2-amine, (1E) and (1Z)-N-methyl-1-(3-pyridyl)-1-octen-4-amine, (1E) and (1Z)-N-methyl-1-(3-pyridyl)-5-methyl-1-hepten-4-amine, (5E) and (5Z)-N-methyl-6-(3-pyridyl)-5-methyl-5-hexen-2-amine, (5E) and (5Z)-N-methyl-6-(3-pyridyl)-5-hexen-2-amine, (5E) and (5Z)-N-methyl-6-(3-pyridyl)-5-methyl-5-hexen-3-amine, (3E) and (3Z)-4-(3-pyridyl)-2-methyl-3-buten-1-amine, (3E) and (3Z)-4-(3-pyridyl)-3-methyl-3-buten-1-amine, (5E) and (5Z)-6-(3-pyridyl)-5-hexen-3-amine, (4E) and (4Z)-5-(3-pyridyl)-2-methyl-4-penten-2-amine, (4E) and (4Z)-5-(3-pyridyl)-3-methyl-4-penten-2-amine, (4E) and (4Z)-5-(3-pyridyl)-4-penten-2-amine, (4E) and (4Z)-5-(3-pyridyl)-1,1,1-trifluoro-4-penten-2-amine, (4E) and (4Z)-5-(3-pyridyl)-4-methyl-4-penten-1-amine, (4E) and (4Z)-5-(3-pyridyl)-4-methyl-4-penten-2-amine, (1E) and (1Z)-1-(3-pyridyl)-1-octen-4-amine, (5E) and (5Z)-6-(3-pyridyl)-5-methyl-5-hexen-2-amine, (5E) and (5Z)-6-(3-pyridyl)-5-hexen-2-amine, and (5E) and (5Z)-6-(3-pyridyl)-5-methyl-5-hexen-3-amine. See, U.S. Pat. No. 5,616,716 to Dull et al. the disclosure of which is incorporated herein in its entirety. Other representative compounds are set forth in U.S. Pat. No. 5,212,188 to Caldwell et al., the disclosure of which is incorporated herein in its entirety, U.S. Pat. No. 5,663,356 to Crooks et al., U.S. Pat. No. 5,663,356 to Reucroft et al, U.S. Pat. No. 5,811,442 to Bencherif et al., and U.S. Pat. No. 5,861,423 to Caldwell et al.

The manner in which aryl substituted olefinic amine compounds useful in the present invention are synthetically produced can vary. (E)-metanicotine-type compounds can be prepared using the techniques set forth by Löffler et al., *Chem. Ber.*, 42, pp. 3431–3438 (1909) and Laforge, *J.A.C.S.*, 50, p. 2477 (1928) from substituted nicotine-type compounds. Certain 6-substituted metanicotine-type compounds can be prepared from the corresponding 6-substituted nicotine-type compounds using the general methods of Acheson et al., *J. Chem. Soc., Perkin Trans.* 1, 2, pp. 579–585 (1980). The requisite precursors for such compounds, 6-substituted nicotine-type compounds, can be synthesized from 6-substituted nicotinic acid esters using the general methods disclosed by Rondahl, *Acta Pharm. Suec.*, 14, pp 113–118 (1977). Preparation of certain 5-substituted metanicotine-type compounds can be accomplished from the corresponding 5-substituted nicotine-type compounds using the general method taught by Acheson et al., *J. Chem. Soc., Perkin Trans.* 1, 2, pp. 579–585 (1980). The 5-halosubstituted nicotine-type compounds (e.g., fluoro- and bromo-substituted nicotine-type compounds) and the 5-amino nicotine-type compounds can be prepared using the general procedures disclosed by Rondahl, *Act. Pharm. Suec.*, 14, pp. 113–118 (1977). The 5-trifluoromethyl nicotine-type compounds can be prepared using the techniques and materials set forth in Ashimori et al., *Chem. Pharm. Bull.*, 38(9), pp. 2446–2458 (1990) and Rondahl, *Acta Pharm. Suec.*, 14, pp.113–118 (1977).

Furthermore, preparation of certain metanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, certain metanicotine-type compounds can be prepared by subjecting a 3-halo-substituted, 5-substituted pyridine compound or a 5-halo-substituted pyrimidine compound to a palladium catalyzed coupling reaction using an olefin possessing a protected amine functionality (e.g., such an olefin provided by the reaction of a phthalimide salt with 3-halo-1-propene, 4-halo-1-butene, 5-halo-1-pentene or 6-halo-1-hexene). See, Frank et al., *J. Org. Chem.*, 43(15), pp. 2947–2949 (1978) and Malek et al., *J. Org. Chem.*, 47, pp. 5395–5397 (1982). Alternatively, certain metanicotine-type compounds can be prepared by coupling an N-protected, modified amino acid residue, such as 4-(N-methyl-N-tert-butyloxycarbonyl)aminobutyric acid methyl ester, with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group then affords the desired metanicotine-type compound.

There are a number of different methods for providing (Z)-metanicotine-type compounds. In one method, (Z)-metanicotine-type compounds can be synthesized from nicotine-type compounds as a mixture of E and Z isomers;

and the (Z)-metanicotine-type compounds can then be separated by chromatography using the types of techniques disclosed by Sprouse et al., Abstracts of Papers, p. 32, Coresta/TCRC Joint Conference (1972). In another method, metanicotine-type compounds can be prepared by the controlled hydrogenation of the corresponding acetylenic compound (e.g., an N-methyl-4-(3-pyridinyl)-3-butyn-1-amine type compound). For example, certain 5-substituted (Z)-metanicotine type compounds and certain 6-substituted (Z)-metanicotine-type compounds can be prepared from 5-substituted-3-pyridinecarboxaldehydes and 6-substituted-3-pyridinecarboxaldehydes, respectively. Representative synthetic techniques for (Z)-metanicotine-type compounds are set forth in U.S. Pat. No. 5,597,919 to Dull et al.

There are a number of methods by which the (Z)-olefinic isomers of aryl substituted olefinic amine compounds can be synthetically produced. In one approach, the (Z)-isomers of aryl substituted olefinic amine compounds can be prepared by the controlled hydrogenation of the corresponding alkynyl compounds (e.g., a N-methyl-5-(3-pyridyl)-4-butyn-2-amine-type compound) using commercially available Lindlar catalyst (Aldrich Chemical Company) using the methodology set forth in H. Lindlar et al., *Org. Syn.* 46: 89 (1966). The requisite alkynyl compounds can be prepared by the palladium catalyzed coupling of an aromatic halide, preferably a 3-bromopyridine-type or a 3-iodopyridine-type compound with an alkynyl side chain compound (e.g., an N-methyl-4-pentyn-2-amine-type compound). Typically the methodolgy set forth in L. Bleicher et al., *Synlett.* 1115 (1995) is used for the palladium catalyzed coupling of an aryl halide with a monosubstituted alkyne in the presence of copper(I) iodide and triphenylphosphine and potassium carbonate as a base. Alkynyl compounds such as N-methyl-4-pentyn-2-amine can be prepared from commercially available 4-pentyn-2-ol (Aldrich Chemical Company) by treatment with p-toluenesulfonyl chloride in pyridine, followed by reaction of the resulting 4-pentyn-2-ol p-toluenesulfonate with excess methylamine either as a 40% aqueous solution or as a 2.0 M solution in tetrahydrofuran. In some instances it may be necessary to protect the amino functionality of the N-methyl-4-pentyn-2-amine-type compound by treatment with di-tert-butyl dicarbonate to give the tert-butoxycarbonyl protected amine-type compound. Such protected amine compounds may undergo the palladium catalyzed coupling with aryl halides and the subsequent controlled hydrogenation of the resulting alkynyl compound more easily than the unprotected amine compounds. The tert-butoxycarbonyl protecting group can be easily removed using a strong acid such as trifluoroacetic acid to yield the (Z)-olefinic isomers of aryl substituted olefinic amine compounds.

The methods by which aryl substituted olefinic amine compounds can be synthetically produced can vary. An olefinic alcohol, such as 4-penten-2-ol, is condensed with an aromatic halide, such as 3-bromopyridine or 3-iodopyridine. typically, the types of procedures set forth in Frank et al., *J. Org. Chem.*, 43, pp. 2947–2949 (1978) and Malek et al., *J. Org. Chem.*, 47, pp. 5395–5397 (1982) involving a palladium-catalyzed coupling of an olefin and an aromatic halide are used. The olefinic alcohol optionally can be protected as a t-butyidimethylsilyl ether prior to the coupling. Desilylation then produces the olefinic alcohol. The alcohol condensation product then is converted to an amine using the type of procedures set forth in deCosta et al., *J. Org. Chem.*, 35, pp. 43344343 (1992). Typically, the alcohol condensation product is converted to the aryl substituted olefinic amine by activation of the alcohol using methanesulfonyl chloride or p-toluenesulfonyl chloride, followed by mesylate or tosylate displacement using ammonia, or a primary or secondary amine. Thus, when the amine is ammonia, an aryl substituted olefinic primary amine compound is provided; when the amine is a primary amine such as methylamine or cyclobutylamine, an aryl substituted olefinic secondary amine compound is provided; and when the amine is a secondary amine such as dimethylamine or pyrrolidine, an aryl substituted olefinic tertiary amine compound is provided. Other representative olefinic alcohols include 4-penten-1-ol, 5-hexen-2-ol, 5-hexen-3-ol, 3-methyl-3-buten-1-ol, 2-methyl-3-buten-1-ol, 4-methyl-4-penten-1-ol, 4-methyl-4-penten-2-ol, 1-octen-4-ol, 5-methyl-1-hepten-4-ol, 4-methyl-5-hexen-2-ol, 5-methyl-5-hexen-2-ol, 5-hexen-2-ol and 5-methyl-5-hexen-3-ol. Trifluormethyl-substituted olefinic alcohols, such as 1,1,1-trifluoro-4-penten-2-ol, can be prepared from 1-ethoxy-2,2,2-trifluoro-ethanol and allyltrimethylsilane using the procedures of Kubota et al., *Tetrahedron Letters*, Vol. 33(10), pp. 1351–1354 (1992), or from trifluoroacetic acid ethyl ester and allyltributylstannane using the procedures of Ishihara et al., *Tetrahedron Letters*, Vol. 34(56), pp. 5777–5780 (1993). Certain olefinic alcohols are optically active, and can be used as enantiomeric mixtures or as pure enantiomers in order to provide the corresponding optically active forms of aryl substituted olefinic amine compounds. When an olefinic allylic alcohol, such as methallyl alcohol, is reacted with an aromatic halide, an aryl substituted olefinic aldehyde is produced; and the resulting aldehyde can be converted to an aryl substituted olefinic amine compound by reductive amination (e.g., by treatment using an alkyl amine and sodium cyanoborohydride). Preferred aromatic halides are 3-bromopyridine-type compounds and 3-iodopyridine-type compounds. Typically, substituent groups of such 3-halopyridine-type compounds are such that those groups can survive contact with those chemicals (e.g., tosylchloride and methylamine) and the reaction conditions experienced during the preparation of the aryl substituted olefinic amine compound. Alternatively, substituents such as —OH, —NH$_2$ and —SH can be protected as corresponding acyl compounds, or substituents such as —NH$_2$ can be protected as a phthalimide functionality.

The manner in which certain aryl substituted olefinic amine compounds possessing a branched side chain, such as (4E)-N-methyl-5-(5-isopropoxy-3-pyridyl)4-penten-2-amine, are provided can vary. By using one synthetic approach, the latter compound can be synthesized in a convergent manner, in which the side chain, N-methyl-N-(tert-butoxycarbonyl)-4-penten-2-amine is coupled with the 3-substituted 5-halo-substituted pyridine, 5-bromo-3-isopropoxypyridine, under Heck reaction conditions, followed by removal of the tert-butoxycarbonyl protecting group. Typically, the types of procedures set forth in W. C. Frank et al., *J. Org. Chem.* 43: 2947 (1978) and N. J. Malek et al., *J. Org. Chem.* 47: 5395 (1982) involving a palladium-atalyzed coupling of an olefin and an aromatic halide are used. The required N-methyl-N-(tert-butoxycarbonyl)-4-penten-2-amine can be synthesized as follows: (i) Commercially available 4-penten-2-ol (Aldrich Chemical Company, Lancaster Synthesis Inc.) can be treated with p-toluenesulfonyl chloride in pyridine to yield 4-penten-2-ol p-toluenesulfonate, previously described by T. Michel, et al., *Liebigs Ann.* 11: 1811 (1996); (ii) The resulting tosylate can be heated with 20 molar equivalents of methylamine as a 40% aqueous solution to yield N-methyl-4-penten-2-amine; and (iii) The resulting amine, such as previously mentioned by A. Viola et al., *J. Chem. Soc., Chem. Commun.* (21): 1429

(1984), can be allowed to react with 1.2 molar equivalents of di-tert-butyl dicarbonate in dry tetrahydrofuran to yield the side chain, N-methyl-N-(tert-butoxycarbonyl)-4-penten-2-amine. The halo-substituted pyridine, (e.g., 5-bromo-3-isopropoxypyridine) can be synthesized by two different routes. In one preparation, 3,5-dibromopyridine is heated at 140° C. for 14 hours with 2 molar equivalents of potassium isopropoxide in dry isopropanol in the presence of copper powder (5%, w/w of the 3,5-dibromopyridine) in a sealed glass tube to yield 5-bromo-3-isopropoxypyridine. A second preparation of 5-bromo-3-isopropoxypyridine from 5-bromonicotinic acid can be performed as follows: (i) 5-Bromonicotinic acid is converted to 5-bromonicotinamide by treatment with thionyl chloride, followed by reaction of the intermediate acid chloride with aqueous ammonia.; (ii) The resulting 5-bromonicotinamide, previously described by C. V. Greco et al., *J. Heteocyclic Chem.* 7(4): 761 (1970), is subjected to Hofmann degradation by treatment with sodium hydroxide and a 70% solution of calcium hypochlorite; and (iii) The resulting 3-amino-5-bromopyridine, previously described by C. V. Greco et al., *J. Heteocyclic Chem.* 7(4): 761 (1970), can be converted to 5-bromo-3-isopropoxypyridine by diazotization with isoamyl nitrite under acidic conditions, followed by treatment of the intermediate diazonium salt with isopropanol to yield 5-bromo-3-isopropoxypyridine. The palladium-catalyzed coupling of 5-bromo-3-isopropoxypyridine and N-methyl-N-(tert-butoxycarbonyl)4-penten-2-amine is carried out in acetonitrile-triethylamine (2:1, v,v) using a catalyst consisting of 1 mole % palladium(II) acetate and 4 mole % tri-o-tolylphosphine. The reaction can be carried out by heating the components at 80° C. for 20 hours to yield (4E)-N-methyl-N-(tert-butoxycarbonyl)-5-(5-isopropoxy-3-pyridyl)-4-penten-2-amine. Removal of the tert-butoxycarbonyl protecting group can be accomplished by treatment with 30 molar equivalents of trifluoroacetic acid in anisole at 0° C. to afford (4E)-N-methyl-5-(5-isopropoxy-3-pyridyl)-4-penten-2-amine.

The manner in which certain aryl substituted olefinic amine compounds possessing a branched side chain are provided can vary. Using one synthetic approach, a compound such as (4E)-N-methyl-5-(5-methoxy-3-pyridyl)-4-penten-2-amine can be synthesized by coupling a halo-substituted pyridine, 5-bromo-3-methoxypyridine with an olefin containing a secondary alcohol functionality, 4-penten-2-ol, under Heck reaction conditions; and the resulting pyridyl alcohol intermediate can be converted to its p-toluenesulfonate ester, followed by treatment with methylamine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The required halo-substituted pyridine, 5-bromo-3-methoxypyridine is synthesized using methodology similar to that described by H. J. den Hertog et al., *Recl. Trav. Chim. Pays-Bas* 74:1171 (1955), namely by heating 3,5-dibromopyridine with 2.5 molar equivalents of sodium methoxide in dry methanol in the presence of copper powder (5%, w/w of the 3,5-dibromopyridine) in a sealed glass tube at 150° C. for 14 hours to produce 5-bromo-3-methoxypyridine. The resulting 5-bromo-3-methoxypyridine, previously described by D. L. Comins, et al., *J. Org. Chem.* 55: 69 (1990), can be coupled with 4-penten-2-ol in acetonitrile-triethylamine (1.1:1, v/v) using a catalyst consisting of 1 mole % palladium(II) acetate and 4 mole % tri-o-tolylphosphine. The reaction is carried out by heating the components in a sealed glass tube at 140° C. for 14 hours to yield (4E)-N-methyl-5-(5-methoxy-3-pyridyl)-4-penten-2-ol. The resulting alcohol is treated with 2 molar equivalents of p-toluenesulfonyl chloride in dry pyridine at 0° C. to produce (4E)-N-methyl-5-(5-methoxy-3-pyridyl)-4-penten-2-ol p-toluensulfonate. The tosylate intermediate is treated with 120-molar equivalents of methylamine as a 40% aqueous solution, containing a small amount of ethanol as a co-solvent to produce (4E)-N-methyl-5-(5-methoxy-3-pyridyl)-4-penten-2-amine.

The manner in which optically active forms of certain aryl substituted olefinic amine compounds, such as (2S)-(4E)-N-methyl-5-(3-pyridyl)-4-penten-2-amine, are provided can vary. In one synthetic approach, the latter type of compound is synthesized by coupling a halo-substituted pyridine, 3-bromopyridine, with an olefin possessing a chiral, secondary alcohol functionality, (2R)-4-penten-2-ol, under Heck reaction conditions. The resulting chiral pyridyl alcohol intermediate, (2R)-(4E)-5-(3-pyridyl)-4-penten-2-ol is converted to its corresponding p-toluenesulfonate ester, which is subsequently treated with methylamine, resulting in tosylate displacement with inversion of configuration. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an aromatic halide and an olefin are used. The chiral side chain, (2R)-4-penten-2-ol can be prepared by treatment of the chiral epoxide, (R)-(+)-propylene oxide (commercially available from Fluka Chemical Company) with vinylmagnesium bromide in tetrahydrofuran at tow temperatures (−25 to −10° C.) using the general synthetic methodology of A. Kalivretenos, J. K. Stille, and L. S. Hegedus, *J. Org. Chem.* 56: 2883 (1991), to afford (2R)-4-penten-2-ol. The resulting chiral alcohol is subjected to a Heck reaction with 3-bromopyridine in acetonitrile-triethylamine (1:1, v/v) using a catalyst consisting of 1 mole % palladium(II) acetate and 4 mole % trio-tolylphosphine. The reaction is done by heating the components at 140° C. for 14 hours in a sealed glass tube, to produce the Heck reaction product, (2R)-(4E)-5-(3-pyridyl)-4-penten-2-ol. The resulting chiral pyridyl alcohol is treated with 3 molar equivalents of p-toluenesulfonyl chloride in dry pyridine at 0° C., to afford the tosylate intermediate. The p-toluenesulfonate ester is heated with 82 molar equivalents of methylamine as a 40% aqueous solution, containing a small amount of ethanol as a co-solvent, to produce (2S)-(4E)-N-methyl-5-(3-pyridyl)-4-penten-2-amine. In a similar manner, the corresponding aryl substituted olefinic amine enantiomer, such as (2R)-(4E)-N-methyl-5-(3-pyridyl)-4-penten-2-amine, can be synthesized by the Heck coupling of 3-bromopyridine and (2S)-4-penten-2-ol. The resulting intermediate, (2S)-(4E)-5-(3-pyridyl)-4-penten-2-ol, is converted to its p-toluenesulfonate, which is subjected to methylamine displacement. The chiral alcohol, (2S)-4-penten-2-ol, is prepared from (S)-(−)-propylene oxide (commercially available from Aldrich Chemical Company) using a procedure analogous to that described for the preparation of (2R)-4-penten-2-ol from (R)-(+)-propylene oxide as reported by A. Kalivretenos, J. K. Stille, and L. S. Hegedus, *J. Org. Chem.* 56: 2883 (1991).

Other compounds that are of particular interest in carrying out the present invention are the pyridyloxylalkylamines and phenoxyalkylamines, including (3-(3-pyridyloxy)propyl) methylamine, (3-(3-pyridyloxy)propyl)amine, (3-(5-bromo-(3-pyridyloxy)propyl)methylamine, (1-methyl-3-(3-pyridyloxy)propyl)methylamine, (3-(5-ethoxy-(3-pyridyloxy)propyl)methylamine, (3-(6-methyl-(3-pyridyloxy)propyl)methylamine, (3-(5-chloro-(3- pyridyloxy)propyl)methylamine, (3-(2-bromo(3-pyridyloxy)propyl)methylamine, (1-methyl-3-(5-methoxy-(3-pyridyloxy)propyl))methylamine, (4-(3-pyridyloxy)butyl))methylamine, (3-phenoxypropyl)methylamine and (3-(3-aminophenoxy)propyl)methylamine, (3-(4methoxyphenoxy)propyl)-methylamine.

The manner in which certain phenoxyalkylamine compounds useful in the present invention are provided can vary. Certain phenoxyalkylamine compounds can be prepared by the alkylation of phenol with a 1,3-dihalopropane, such as 1,3-dichloropropane, 1,3-dibromopropane, 1,3-diiodopropane, or 1-chloro-3-iodopropane, which are commercially available from Aldrich Chemical Company, in the presence of a base (e.g., sodium hydride) in dry N,N-dimethylformamide. The resulting 3-halo-1-phenoxypropane can be converted to a phenoxyalkylamine, such as methyl(3-phenoxypropyl)amine, by treatment with methylamine in a solvent, such as tetrahydrofuran or aqueous methanol. The manner in which certain 3-substituted-phenyl analogs of (3-phenoxypropyl)methylamine of the present invention can be synthetically prepared is analogous to that described for the preparation of methyl(3-phenoxypropyl)amine with the exception that 3-substituted-phenols are employed rather than phenol. In some instances, protecting groups may be employed when necessary. For example, one representative compound, (3-(3-aminophenoxy)propyl)methylamine can be prepared by the alkylation of an N-phthalamido-protected phenol, 2-(3-hydroxyphenyl)isoindoline-1,3-dione (prepared by treatment of 3-aminophenol with phthalic anhydride) with 1-chloro-3-iodopropane. The resulting intermediate, 2-(3-(3-chloropropoxy)-phenyl)isoindoline-1,3-dione can be converted to (3-(3-aminophenoxy)-propyl)methylamine by treatment with methanolic methylamine. The manner in which certain 4-substituted-phenyl analogs of methyl(3-phenoxypropyl)amine of the present invention can be synthetically prepared is analogous to that described for the preparation of methyl(3-phenoxypropyl)amine with the exception that 4-substituted-phenols are employed rather than phenol. For example, 4-methoxyphenol can be converted to (3-(4-methoxyphenoxy)propyl)methylamine.

The manner by which pyridyloxyalkylamine compounds are provided can vary. Certain pyridyloxyalkylamine compounds can be prepared by the alkylation of 3-hydoxypyridine with a 1,3-dihalopropane, such as 1,3-dichloropropane, 1,3-dibromopropane, 1,3-diodopropane or 1-chloro-3-iodopropane, which are commercially available from Aldrich Chemical Company, in the presence of a base (e.g., sodium hydride) in dry N,N-dimethylformamide. The resulting 3-halo-1-(3-pyridyloxy)propane can be converted to a pyridyloxyalkylamine, such as (3-(3-pyridyloxy)propyl) methylamine, by treatment with methylamine in a solvent, such as tetrahydrofuran or aqueous methanol. One representative compound, (3-(3-pyridyloxy)propyl)methylamine is prepared by the reaction of 3-hydroxypyridine with 1.2 molar equivalents of 1-chloro-3-iodopropane and 1.6 molar equivalents of sodium hydride in dry N,N-dimethylformamide at ambient temperature. The resulting intermediate, 3-chloro-1-(3-pyridyloxy)propane, obtained in about 54% yield, is converted to (3-(3-pyridyloxy)propyl) methylamine in about 40% yield, by treatment with an excess (25 molar equivalents) of aqueous methylamine in methanol, assisted by heating. Certain pyridyloxyalkylamine compounds, such as (4-(3-pyridyloxy)-butyl) methylamine, can be prepared by alkylating 3-hydoxypyridine with a 1,4-dihalobutane, such as 1,4-diiodobutane, 1,4-dibromobutane, 1,4-dichlorobutane or 1-chloro4-iodobutane, which are commercially available from Aldrich Chemical Company, in the presence of a base (e.g., sodium hydride) in N,N-dimethylformamide. The resulting 4-halo-1-(3-pyridyloxy)butane can be converted to a pyridyloxyalkylamine, such as (4-(3-pyridyloxy)butyl) methylamine, by treatment with methylamine in a solvent, such as tetrahydrofuran or aqueous methanol.

The manner by which certain 2-substituted-3-pyridyl analogs of (3-(3-pyridyloxy)propyl)methylamine and certain 6-substituted-3-pyridyl analogs of (3-(3-pyridyloxy)propyl) methylamine can be synthetically prepared is analogous to that described for the preparation of (3-(3-pyridyloxy)-propyl)methylamine with the exception that 2-substituted-3-hydroxypyridines and 6-substituted-3-hydroxypyridines are employed rather than 3-hydroxypyridine. For example, using such methodology, commercially available 2-bromo-3-hydroxypyridine and 3-hydroxy-2-nitropyridine can be converted to 3-(2-bromo(3-pyridyloxy))propyl) methylamine and 3-(2-nitro(3-pyridyloxy))propyl) methylamine, respectively. Similarly, commercially available 3-hydroxy-6-methylpyridine can be converted to 3-(6-methyl(3-pyridyloxy))propyl)methylamine.

The manner by which certain 5-substituted-3-pyridyl analogs of (3-(3-pyridyloxy)propyl)methylamine can be synthesized is analogous to that described for (3-(3-pyridyloxy) propyl)methylamine, with the exception that 5-substituted-3-hydroxypyridines are employed rather than 3-hydroxypyridine. For example, using such a methodology, 5-bromo-3-hydroxypyridine can be converted to the intermediate, 3-chloro-1-(5-bromo-3-pyridyloxy)propane, which is converted to 3-(5-bromo(3-pyridyloxy))-propyl) methylamine. 5-Bromo-3-hydroxypyridine can be prepared form 2-furfurylamine using the procedure described in U.S. Pat. No. 4,192,946 to Clauson-Kaas et al. the disclosure of which is incorporated herein by reference in its entirety. In a similar manner, 5-chloro-3-hydroxypyridine, which is commercially available from Aldrich Chemical Company, can be converted to 3-(5-chloro(3-pyridyloxy))propyl) methylamine. Similarly, 5-methoxy-3-hydroxypyridine, prepared according to the procedures set forth in Chen et al., *Heterocycles* 24(12): 3411 (1986), can be converted to 3-(5-methoxy(3-pyridyloxy))propyl)methylamine. Similarly, 5-ethoxy-3-hydroxypyridine can be converted to 3-(5-ethoxy(3-pyridyloxy))propyl)methylamine. Similarly, 5-amino-3-hydroxypyridine, prepared according to the procedures set forth in Tamura et al., *Heterocycles* 15(2): 871 (1981), can be converted to 3-(5-amino(3-pyridyloxy)) propyl)methylamine. In a similar manner, 3-hydroxy-5-trifluoromethylpyridine and 2-fluoro-5-hydroxy-3-methylpyridine, each prepared using methods set forth in PCT WO 96/40682, can be converted to 3-(5-trifluoromethyl(3-pyridyloxy))propyl)methylamine and 3-(5-fluoro-5-methyl(3-pyridyloxy))propyl)methylamine, respectively.

A number of 5-substituted analogs, such as (3-(5-substituted(3-pyridyloxy))propyl)methylamine, can be synthesized from 5-substituted 3-hydroxypyridines, which can be prepared from 5-amino-3-hydroxypyridine via a diazonium salt intermediate. For example, 5-amino-3-hydroxypyridine can be converted to 5-fluoro-3-hydroxypyridine, 5-chloro-3-hydroxypyridine, 5-bromo-3-hydroxypyridine, 5-iodo-3-hydroxypyridine or 5-cyano-3-hydroxypyridine, using the general techniques set forth in Zwart et al., *Recueil Trav. Chim. Pays-Bas* 74: 1062 (1955). Futhermore, 5-hydroxy-substituted analogs can be prepared from the reaction of the corresponding 5-diazonium salt intermediate with water. The 5-Fluoro-substituted analogs can be prepared from the reaction of the 5-diazonium salt intermediate with fluoroboric acid. 5-Chloro-substituted analogs can be prepared from the reaction of 5-amino-3-hydroxypyridine with sodium nitrite and hydrochloric acid in the presence of copper chloride. The 5-cyano-substituted analogs can be prepared from the reaction of the corresponding diazonium salt intermediate with potassium copper cyanide. The 5-amino-substituted analogs can be converted to the corresponding 5-nitro analogs by reaction with fuming sulfuric acid and peroxide according to the general techniques described in Morisawa, *J. Med. Chem.* 20: 129 (1977), for converting an amino pyridine to a nitropyridine.

Certain pyridyloxyalklylamines that possess a branched side chain, such as (1-methyl-3-(3-pyridyloxy)propyl) methylamine, can be prepared by alkylating 3-hydroxypyridine with a protected 3-hydroxy-1-halobutane, such as 3-[(tert-butyl)dimethylsilyloxy]-1-bromobutane (prepared according to the procedures set forth in Gerlach et al., *Helv. Chim. Acta.* 60(8): 2860 (1977)), thereby producing a (tert-butyl)dimethylsilyl protected 4-(3-pyridyloxy)butan-2-ol. The (tert-butyl)dimethylsilyl group can be removed by treatment with ammonium fluoride or aqueous acetic acid to give 4-(3-pyridyloxy)butan-2-ol. Mesylation or tosylation of that compound with methanesulfonyl chloride in triethylamine or p-toluenesulfonyl chloride in pyridine, followed by treatment with methylamine in tetrahydrofuran or aqueous methanol, provides a compound having a methyl branched side chain (e.g., (1-methyl-3-(3-pyridyloxy)propyl)methylamine).

Alternatively, pyridyloxyalkylamines possessing a branched side chain, such as (1-methyl-3-(3-pyridyloxy)propyl)methylamine, can be synthesized by alkylating 3-hydroxypyridine with a protected 1-iodo-3-butanone, namely 2-methyl-2-(2-iodoethyl)-1,3-dioxolane, with is prepared according to the procedures set forth in Stowell et al., *J. Org. Chem.* 48: 5381 (1983). The resulting ketal, 3-(2-(1-methyl-2,5-dioxolanyl)ethoxy)pyridine, can be protected by treatment with aqueous acetic acid or p-toluenesulfonic acid in methanol to yield 4-(3-pyridyloxy)butan-2-one. Reductive amination of the resulting ketone using methylamine and sodium cyanoborohydride according to the methodology set forth in Borch, *Org. Syn.* 52: 124 (1972) provides (1-methyl-3-(3-pyridyloxy)propyl)methylamine. Alternatively, the intermediate, 4-(3-pyridyloxy)butan-2-one, can be reduced with sodium borohydride to yield an alcohol, 4-(3-pyridyloxy)butan-2ol. Mesylation or tosylation of that alcohol, followed by mesylation or tosylation displacement using methylamine, provides the branched chain pyridyloxyalkylamine, (1-methyl-3-(3-pyridyloxy)propyl)methylamine.

Chiral starting materials are available for the synthesis of the pure enantiomers of the branched chain pyridyloxyalkylamines, such a (1-methyl-3-(3-pyridyloxy)proyl)methylamine. One approach can be carried out using either methyl (R)-(−)-3-hydroxybutyrate or the (+)-enantiomer, (S)-(+)-3-hydroxybutyrate, both of which are available from Aldrich Chemical Company. For example, (R)-(−)-3-hydroxybutyrate can be converted to (R)-(−)-3-tetrahydropyranyloxybutyl bromide, using the procedures set forth in Yuasa et al., *J. Chem. Soc., Perk. Trans.* 1(5): 465 (1996). Alkylation of 3-hyroxypyridine with (R)-(−)-3-tetrahydropyranyloxybutyl bromide using sodium hydride in N,N-dimethylformamide produces the tetrahydropyranyl ether of 4-(3-pyridyloxy)butan-2R-ol. Removal of the tetrahydropyranyl protecting group of that compound using p-toluenesulfonic acid monohydrate in methanol affords 4-(3-pyridyloxy)butan-2R-ol. The resulting chiral alcohol can be elaborated to the chiral pyridyloxyalkylamine, (1S-3-(3-pyridyloxy)propyl)methylamine using a two-step sequence involving tosylation and methylamine displacement of the intermediate tosylate. In a similar process, (S)-(+)-3-hydroxybutyrate can be converted to (S)-(+)-3-tetrahydropyranyloxybutyl bromide using the procedures set forth in Sakai et al., *Agric. Biol. Chem.* 50(6): 1621 (1986). This protected bromo alcohol can be converted to the corresponding chiral pyridyloxyalkylamine, methyl(1R-3-(3-pyridyloxy)propyl)amine, using a sequence involving alkylation of 3-hydroxypyridine, removal of the tetrahydropyranyl group, tosylation, and methylamine displacement of the intermediate tosylate.

Certain other compounds of interest in carrying out the present invention include aryl substituted amine compounds, such as 3-aminophenyl amine compounds. Representative compounds include (E)-4-(3-aminophenyl)-3-buten-1-amine, (E)-N-methyl-4-(3-aminophenyl)-3-buten-1-amine and (E)-N-methyl-5-(3-aminophenyl)-3-penten-2-amine.

The methods by which certain other compounds useful in carrying out the present invention can be synthetically produced can vary. Certain aryl substituted olefinic amine compounds can be prepared using a palladium catalyzed coupling reaction of an aromatic halide and a terminal olefin containing a protected amine substituent (e.g., phthaloyl, benzoyl, or tert-butoxycarbonyl protecting groups), removal of the protective group to obtain a primary amine, and optional alkylation to provide a secondary or tertiary amine. In particular, certain compounds, such as (E)-4-(3-aminophenyl)-3-buten-1-amine can be prepared by subjecting a 3-halo-substituted aniline compound such as 3-bromoaniline or 3-iodoaniline (commercially available from Aldrich Chemical Company and Lancaster Synthesis, Inc.) to a palladium catalyzed Heck coupling reaction using an olefin possessing a protected amine functionality (e.g., such an olefin provided by the reaction of a phthalimide salt with 4-halo-1-butene), followed by removal of the phthaloyl protecting group with methylamine or hydrazine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. In a similar manner, other compounds can be prepared by the Heck reaction of 3-halo-substituted aniline compounds with an olefin containing a protected amine functionality, (such as provided by the reaction of a phthalimide salt with 3-halo-1-propene, 5-halo-1-pentene or 6-halo-1-hexene), followed by removal of the phthaloyl protecting group with methylamine or hydrazine. Primary amines, produced in these procedures, may be alkylated by sequential reaction with di-tert-butyl dicarbonate (to give the N-tert-butoxycarbonyl derivatives), and followed by reaction with sodium hydride and an alkyl halide (e.g., methyl iodide, benzyl bromide, propargyl bromide) in N,N-dimethylformamide, as described by Dull in U.S. Pat. No. 5,597,919. Removal of the tert-butoxycarbonyl group with trifluoroacetic acid will give the secondary amine (i.e., the corresponding N-methyl, N-benzyl, or N-propargyl derivative).

In a similar approach, other compounds such as (E)-N-methyl-4-(3-aminophenyl)-3-buten-1-amine can be prepared by subjecting a 3-halo-substituted aniline such as 3-bromoaniline or 3-iodoaniline to a palladium catalyzed coupling reaction with an olefin possessing a protected amine functionality (e.g., such as N-methyl-N-(3-buten-1-yl)benzamide), followed by removal of the benzoyl protecting group with aqueous acid. The required olefin can be prepared by reacting 4-bromo-1-butene with an excess of condensed methylamine in N,N-dimethylformamide in the presence of potassium carbonate to give N-methyl-3-buten-1-amine. Treatment of the latter compound with benzoyl chloride in dichloromethane containing triethylamine affords the olefinic side chain, N-methyl-N-(3-buten-1-yl) benzamide.

In another approach, other compounds such as (E)-N-methyl-4-(3-aminophenyl)-3-buten-1-amine can be prepared by subjecting a 3-halo-substituted aniline such as 3-bromoaniline or 3-iodoaniline to a palladium catalyzed coupling reaction with an olefin possessing a protected amine functionality (e.g., such as N-methyl-N-(tert-butoxycarbonyl)-3-buten-1-amine), followed by removal of the tert-butoxycarbonyl protecting group with trifluoroacetic acid. The required olefin, N-methyl-N-(tert-butoxycarbonyl)-3-buten-1-amine can be prepared by reacting 4-bromo-1-butene with an excess of condensed methylamine in N,N-dimethylformamide in the presence of potassium carbonate to give N-methyl-3-buten-1-amine. The latter compound can be treated with one equivalent of di-tert-butyldicarbonate in tetrahydrofuran to give N-methyl-N-(tert-butoxycarbonyl)-3-buten-1-amine.

The manner in which certain aryl substituted olefinic amine compounds possessing a branched side chain, such as (E)-N-methyl-5-(3-aminophenyl)-4-penten-2-amine, are provided can vary. By using one synthetic approach, the compound can be synthesized in a convergent manner, in which the side chain, N-methyl-N-(tert-butoxycarbonyl)-4-penten-2-amine is coupled with a 3-halo-substituted aniline, such as 3-bromoaniline (N-protected with the phthaloyl group), under Heck reaction conditions, followed by removal of the tert-butoxycarbonyl protecting group with trifluoroacetic acid and then removal of the phthaloyl protecting group with methylamine. The required olefin, N-methyl-N-(tert-butoxycarbonyl)-4-penten-2-amine can be prepared by treatment of commercially available 4-penten-2-ol (Aldrich Chemical Company, Lancaster Synthesis Inc) with p-toluenesulfonyl chloride in pyridine to afford 4-penten-2-ol p-toluenesulfonate, previously described by T. Michel, et al., *Liebigs Ann.* 11: 1811 (1996). The resulting tosylate can be converted to N-methyl-4-penten-2-amine by heating with excess methylamine. The latter amine, previously mentioned by A. Viola et al., *J. Chem. Soc., Chem. Commun.* (21): 1429 (1984), can be converted to the olefinic amine side chain, N-methyl-N-(tert-butoxycarbonyl)-4-penten-2-amine by treatment with di-tert-butyl dicarbonate in dry tetrahydrofuran.

The aniline nitrogen can also be alkylated using the coupling method of O. Mitsunobu, *Synthesis:* 1 (1981). Any primary or secondary alcohol, including those containing other functional groups, may be used in the coupling. As an example, reaction of 3-bromoaniline with 3quinuclidinol (Aldrich Chemical Company) in the presence of triphenylphosphine and diethyl azodicarboxylate will result in the formation of 3-bromo-N-(3-quinuclidinyl)aniline, which can be used in Heck couplings as described above.

Using the previously described synthetic methods involving the Heck reaction, certain N-alkyl-3-aminophenyl substituted olefinic amine compounds such as (E)-N-methyl-4-(N-methyl-3-aminophenyl)-4-buten-1-amine can be prepared starting from 3-halo-N-alkylanilines such as 3-iodo-N-methyl-aniline. The latter compound can be prepared from commercially available 3-iodoaniline (Aldrich Chemical Company, Lancaster Synthesis, Inc.) using the techniques of S. Padmanabhan et al., *Synth. Commun.* 27:691–699 (1997). 3-Iodoaniline can be monomethylated using trimethyl orthoformate in the presence of concentrated sulfuric acid followed by acid hydrolysis to give 3-iodo-N-methyl-aniline. Certain N,N-dialkyl-3-aminophenyl substituted olefinic amine compounds such as (E)-N-methyl-4-(N,N-dimethyl-3-aminophenyl)-4-buten-1-amine can be prepared starting from 3-bromo-N,N-dimethyl-aniline, which is commercially available from Karl Industries and Lancaster Synthesis, Inc.

Alternatively, an olefinic alcohol, such as 3-buten-1-ol, can be condensed with an aromatic halide, such as 3-bromoaniline or 3-iodoaniline. Protection of the nitrogen functionality of the aniline compound can be provided by a phthaloyl protecting group, using phthalic anhydride. Typically, the types of procedures set forth in Frank et al., *J. Org. Chem.* 43: 2947–2949 (1978) and Malek et al., *J. Org. Chem.* 47: 5395–5397 (1982) involving a palladium-catalyzed coupling of an olefin and an aromatic halide are used. The olefinic alcohol optionally can be protected as a tert-butyldimethylsilyl ether prior to the coupling. Desilylation then produces the olefinic alcohol. The alcohol condensation product then is converted to an amine using the type of procedures set forth in deCosta et al., *J. Org. Chem.*, 35: 4334–4343 (1992). Typically, the alcohol condensation product is converted to the aryl substituted olefinic amine by activation of the alcohol using methanesulfonyl chloride or p-toluenesulfonyl chloride, followed by mesylate or tosylate displacement using ammonia, or a primary or secondary amine. Thus, when the amine is ammonia, an aryl substituted olefinic primary amine compound is provided; when the amine is a primary amine such as methylamine or cyclobutylamine, an aryl substituted olefinic secondary amine compound is provided; and when the amine is a secondary amine such as dimethylamine or pyrrolidine, an aryl substituted olefinic tertiary amine compound is provided. Other representative olefinic alcohols include 4-penten-1-ol, 5-hexen-2-ol, 5-hexen-3-ol, 3-methyl-3-buten-1-ol, 2-methyl-3-buten-1-ol, 4-methyl-4-penten-1-ol, 4-methyl-4-penten-2-ol, 1-octen-4-ol, 5-methyl-1-hepten-4ol, 4-methyl-5-hexen-2-ol, 5-methyl-5-hexen-2-ol, 5-hexen-2-ol and 5-methyl-5-hexen-3-ol. Trifluoromethyl-substituted olefinic alcohols, such as 1,1,1-trifluoro-4-penten-2-ol, can be prepared from 1-ethoxy-2,2,2-trifluoroethanol and allyltrimethylsilane using the procedures of Kubota et al., *Tetrahedron Lett.* 33(10): 1351–1354 (1992), or from trifluoroacetic acid ethyl ester and allyltributylstannane using the procedures of Ishihara et al., *Tetrahedron Lett.* 34(56): 5777–5780 (1993). Certain olefinic alcohols are optically active, and can be used as enantiomeric mixtures or as pure enantiomers in order to provide the corresponding optically active forms of aryl substituted olefinic amine compounds. When an olefinic allylic alcohol, such as methallyl alcohol, is reacted with an aromatic halide, an aryl substituted olefinic aldehyde is produced; and the resulting aldehyde can be converted to an aryl substituted olefinic amine compound by reductive amination (e.g., by treatment using an alkyl amine and sodium cyanoborohydride). Typically, substituent groups of such 3-halo-aniline-type compounds are such that those groups can survive contact with those chemicals (e.g., tosyl chloride and methylamine) and the reaction conditions experienced during the preparation of the aryl substituted olefinic amine compound. Alternatively, substituents such as —OH, —NH$_2$ and —SH can be protected as corresponding acyl compounds, or substituents such as —NH$_2$ can be protected as a phthalimide functionality.

Certain 5-alkoxy-3-aminophenyl substituted olefinic amine compounds, such as (E)-N-methyl-5-(5-methoxy-3-aminophenyl)-4-penten-2-amine, can be synthesized by coupling a 3-halo-5-alkoxyaniline such as 3-bromo-5-methoxyaniline or 3-iodo-5-methoxyaniline (protected by a phthaloyl functionality) with an olefin containing a secondary alcohol functionality, 4-penten-2-ol, under Heck reaction conditions. The resulting secondary alcohol intermediate can be converted to its p-toluenesulfonate ester, followed by treatment with methylamine (which also removes the protecting group). Alternatively, certain 5-alkoxy-3-aminophenyl substituted olefinic amine compounds can be synthesized by coupling a 3-halo-5-alkoxyaniline such as 3-bromo-5-methoxyaniline or 3-iodo-5-methoxyaniline (protected by a phthaloyl functionality) with an olefinic side chain compound, such as N-methyl-N-(tert-butoxycarbonyl)-4-penten-2-amine, followed by removal of the protecting groups. The required 3-halo-5-alkoxyaniline compounds such as 3-bromo-5-methoxyaniline and 3-iodo-5-methoxyaniline can be prepared using the techniques of T. A. Emokpae et al., *J. Chem. Soc., Perkin Trans* 2 (1):14–17 (1977) and B. Liedholm, *Acta Chem. Scand., Ser. B* 38:877–884 (1984). In the former method, 3-bromo-5-methoxyaniline and 3-iodo-5-methoxyaniline can be prepared starting from commercially available 1,3,5-trinitrobenzene. Treatment of the latter compound with refluxing sodium methoxide produces 3,5-dinitroanisole. One of the nitro groups is then reduced to give 3-methoxy-5-nitroaniline. The latter compound can be diazotized and treated with copper(I) bromide to give 1-bromo-3-methoxy-5-nitrobenzene. Reduction with tin and hydrochloric acid gives 3-bromo-5-methoxyaniline. In a similar manner, 3-iodo-5-methoxyaniline can be prepared by diazotizing 3-methoxy-5-nitroaniline to give 1-iodo-3-methoxy-5-nitrobenzene. The latter compound can be reduced with iron filings and hydrochloric acid to give 3-iodo-5-methoxyaniline. Other 3-halo-5-alkoxyanilines such as 3-bromo-5-ethoxyaniline, 3-bromo-5-isopropoxyaniline, and 3-bromo-5-sec-butoxyaniline can be prepared using similar techniques. As such, compounds of the present invention such as (E)-N-methyl-5-(5-ethoxy-3-aminophenyl)-4-penten-2-amine, (E)-N-methyl-5-(5-isopropoxy-3-aminophenyl)-4-penten-2-amine, and (E)-N-methyl-5-(5-sec-butoxy-3-aminophenyl)-4-penten-2-amine can be similarly prepared.

The manner in which optically active forms of certain aryl substituted olefinic amine compounds, such as (2S)-(4E)-N-methyl-5-(3-aminophenyl)-4-penten-2-amine, are provided can vary. In one synthetic approach, such compounds can be synthesized by coupling a halo-substituted aniline, 3-bromoaniline (which is protected with an appropriate protecting group, such as a phthaloyl group), with an olefin possessing a chiral, secondary alcohol functionality, (2R)-4-penten-2-ol, under Heck reaction conditions (acetonitrile-triethylamine (1:1, v/v) using a catalyst consisting of 1 mole % palladium(II) acetate and 4 mole % tri-o-tolylphosphine). The resulting chiral alcohol intermediate, (2R)-(4E)-5-(N-phthaloyl-3-aminophenyl)-4-penten-2-ol can be converted to its corresponding p-toluenesulfonate ester, which can be subsequently treated with excess methylamine, resulting in tosylate displacement with inversion of configuration to give the chiral amine, (2S)-(4E)-N-methyl-5-(3-aminophenyl)-4-penten-2-amine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an aromatic halide and an olefin are used. The chiral side chain, (2R)-4-penten-2-ol can be prepared by treatment of the chiral epoxide, (R)-(+)-propylene oxide (commercially available from Fluka Chemical Company) with vinylmagnesium bromide in tetrahydrofuran at low temperatures (−25 to −10° C.) using the general synthetic methodology of Kalivretenos et al., *J. Org. Chem.* 56: 2883 (1991), to afford (2R)-4-penten-2-ol.

In a similar manner, the corresponding aryl substituted olefinic amine enantiomer, such as (2R)-(4E)-N-methyl-5-(3-aminophenyl)-4-penten-2-amine, can be synthesized by the Heck coupling of 3-bromoaniline and (2S)-4-penten-2-ol. The resulting intermediate, (2S)-(4E)-5-(3-aminophenyl)-4-penten-2-ol, can be converted to its p-toluenesulfonate, which is subjected to methylamine displacement. The chiral alcohol, (2S)-4-penten-2-ol, can be prepared from (S)-(−)-propylene oxide (commercially available from Aldrich Chemical Company) using a procedure analogous to that described for the preparation of (2R)-4-penten-2-ol from (R)-(+)-propylene oxide as reported by Kalivretenos et al., *J. Org. Chem.* 56: 2883 (1991).

Certain aryl substituted olefinic amine compounds can be prepared by coupling an N-protected, modified amino acid residue, such as 4-(N-methyl-N-tert-butyloxycarbonyl) aminobutyric acid methyl ester, with an aryl lithium compound, as can be derived from a suitable aryl halide and an alkyl lithium such as butyl lithium. The resulting N-protected aryl ketone is then chemically reduced to the corresponding alcohol, converted to the alkyl halide, mesylate or tosylate, and subsequently dehydrohalogenated or otherwise eliminated to introduce the olefin functionality. Removal of the N-protecting group then affords the desired compound.

Alternatively, the aryl substituted olefinic amine compounds can be prepared by coupling an N-protected aminoaldehyde, such as 4-(N-methyl-N-(tert-butoxycarbonyl)amino)pentanal with an aryllithium. The required aldehyde can be prepared according procedure described by Otsuka et al., *J. Am Chem. Soc.* 112: 838–845 (1990), starting from commercially available 1,5-dimethyl-2-pyrrolidinone (Aldrich Chemical Company). Thus, heating 1,5-dimethyl-2-pyrrolidinone with 6N hydrochloric acid forms 4-(methylamino)pentanoic acid, which can be readily esterified to ethyl 4-(methylamino)pentanoate. The latter compound can be treated with one equivalent of di-tert-butyl dicarbonate to give ethyl 4-(N-methyl-N-(tert-butoxycarbonyl)amino)pentanoate which is then reduced with DIBAL-H to give 4-(N-methyl-N-(tert-butoxycarbonyl)amino)pentanal. Reaction of this aldehyde with an aryllithium will generate an alcohol, which can subsequently be converted to the N-protected olefinic amine by the procedures mentioned above (conversion of the alcohol to the halide and subsequent dehydrohalogenation). Removal of the tert-butoxycarbonyl protecting group affords the desired (E)-5-aryl-4-penten-2-amine. Suitably protected 3-haloanilines can be used as precursors of the aryllithiums required for this process, as described by Guijarro et al., *Tetrahedron* 49: 469–82 (1992) and by Gross et al., *J. Org. Chem.* 58, 2104–9 (1993). Thus 3-chloroaniline can be treated sequentially with pivaloyl chloride, n-butyllithium, and lithium in the presence of catalytic naphthalene to give a pivaloyl protected 3-(aminophenyl)lithium. This aryllithium, upon condensation with 4-(N-methyl-N-(tert-butoxycarbonyl)amino)pentanal and subsequent conversion of the alcohol into the alkene (as described above) and removal of the protecting groups, gives (E)-N-methyl-5-(3-aminophenyl)-4-penten-2-amine.

Aryl substituted olefinic amines may contain azacyclic functionality, such as pyrrolidine or quinuclidine. The methods of synthesis of such compounds may vary. In one method, a Heck coupling can be used to attach a vinyl or allyl substituted nitrogen heterocycle to a 3-haloaniline.

Thus N-(tert-butoxycarbonyl)-2-allylpyrrolidine and 3-bromoaniline can be coupled under conditions described by W. C. Frank et al., *J. Org. Chem.* 43: 2947 (1978) and N. J. Malek et al., *J. Org. Chem.* 47: 5395 (1982) involving palladium catalysis. Removal of the protecting group, using trifluoroacetic acid, will give 2-(1-(3-aminophenyl)propen-3-yl)pyrrolidine. The requisite N-(tert-butoxycarbonyl)-2-allylpyrrolidine can be made from commercially available 2-pyrrolidinemethanol (Aldrich Chemical Company). Treatment of 2-pyrrolidinemethanol with di-tert-butyl dicarbonate results in protection of the amine as its tert-butoxycarbonyl derivative. Subsequent reaction with p-toluenesulfonyl chloride in pyridine, followed by sodium iodide in acetone, gives 2-(iodomethyl)-N-(tert-butoxycarbonyl)pyrrolidine. This can be coupled with vinylmagnesium in the presence of cuprous iodide to give N-(tert-butoxycarbonyl)-2-allylpyrrolidine. The use of enantiomerically pure 2-pyrrolidinemethanol (both R and S isomers are available from Aldrich Chemical Company) results in the production of the single enantiomer of N-(tert-butoxycarbonyl)-2-allylpyrrolidine.

Likewise, 2-allylquinuclidine can be coupled with 3-bromoaniline, under Heck conditions, to give 2-(1-(3-aminophenyl)propen-3-yl)quinuclidine. The required 2-allylquinuclidine can be produced from 3-quinuclidinone (Aldrich Chemical Company) by alkylation and deoxygenation. Thus, 3-quinuclidinone is converted into its isopropylimine with isopropylamine and molecular sieves. Treatment of the imine with lithium diisopropylamide and allyl bromide, followed by hydrolysis, gives 2-allyl-3-quinuclidinone. Deoxygenation, by conversion of the ketone into its p-toluenesulfonylhydrazone and reduction with sodium borohydride, gives 2-allylquinuclidinone.

There are a number of methods by which the (Z)-olefinic isomers of aryl substituted olefinic amine compounds can be synthetically produced. In one approach, the (Z)-isomers of aryl substituted olefinic amine compounds can be prepared by the controlled hydrogenation of the corresponding alkynyl compounds (e.g., a N-methyl-5-(3-aminophenyl)-4-butyn-2-amine-type compound) using commercially available Lindlar catalyst (Aldrich Chemical Company) using the methodology set forth in H. Lindlar et al., *Org. Syn.* 46: 89 (1966). The requisite alkynyl compounds can be prepared by the palladium catalyzed coupling of an aromatic halide, preferably a 3-bromoaniline-type or a 3-iodoaniline-type compound with an alkynyl side chain compound (e.g., an N-methyl-4-pentyn-2-amine-type compound). Typically the methodology set forth in L. Bleicher et al., *Synlett.* 1115 (1995) is used for the palladium catalyzed coupling of an aryl halide with a monosubstituted alkyne in the presence of copper(I) iodide and triphenylphosphine and potassium carbonate as a base. Alkynyl compounds such as N-methyl-4-pentyn-2-amine can be prepared from commercially available 4-pentyn-2-ol (Aldrich Chemical Company) by treatment with p-toluenesulfonyl chloride in pyridine, followed by reaction of the resulting 4-pentyn-2-ol p-toluenesulfonate with excess methylamine either as a 40% aqueous solution or as a 2.0 M solution in tetrahydrofuran. In some instances it may be necessary to protect the amino functionality of the N-methyl-4-pentyn-2-amine-type compound by treatment with di-tert-butyl dicarbonate to give the tert-butoxycarbonyl protected amine-type compound. Such protected amine compounds may undergo the palladium catalyzed coupling with aryl halides and the subsequent controlled hydrogenation of the resulting alkynyl compound more easily than the unprotected amine compounds. The tert-butoxycarbonyl protecting group can be easily removed using a strong acid such as trifluoroacetic acid to yield the (Z)-olefinic isomers of aryl substituted olefinic amine compounds.

The manner in which aryl substituted acetylenic amine compounds are synthetically produced can vary. For example, an aryl substituted acetylenic amine compound, such as an N-methyl-4-(3,4-dimethoxyphenyl)-3-butyn-1-amine type compound, can be prepared using a number of synthetic steps: (i) conversion of 3,4-dimethoxybenzaldehyde to a 1,1-dihalo-2-(3,4-dimethoxyphenyl)-ethylene using a carbon tetrahalide and triphenylphosphine; (ii) side chain elaboration of this intermediate by reaction with butyl lithium and ethylene oxide, affording 4-(3,4-dimethoxyphenyl)-3-butyn-1-ol; and (iii) conversion of this intermediate to its methanesulfonate ester or p-toluenesulfonate ester, and (iv) mesylate or tosylate displacement with methyl amine, affording an N-methyl-4-(3,4-dimethoxyphenyl)-3-butyn-1-amine type compound. Representative alkylene oxides which can be employed either in racemic or optically active form include propylene oxide, 1,2-epoxybutane, 1,2-epoxypentane, 1,2-epoxyhexane, (E)-2,3-epoxybutane, and (Z)-2,3-epoxybutane. Other substituted benzaldehydes, such as 3-methoxybenzaldehyde, can be employed and other substituted aromatic aldehydes can be used. By the controlled hydrogenation of the alkynyl compounds using commercially available Lindlar catalyst using the methodology previously described, the (Z)-isomers of aryl substituted olefinic amine compounds can be obtained.

Certain compounds, with alkyl or aryl substitution on one or both of the olefinic carbons, can be made by a variety of methods. For instance, the Wittig reaction of an alkyl aryl ketone with an (aminoalkyl)triphenylphosphoniumylide will give an aryl substituted alkenamine. In one illustration of this chemistry, (3-bromopropyl)triphenylphosphonium bromide (Aldrich Chemical Company) can be reacted with a variety of primary and secondary amines to give the (3-(N-alkylamino)propyl)triphenylphosphonium bromides and (3-(N,N-dialkylamino)propyl)triphenylphosphonium bromides. These can be treated with n-butyllithium to generate the corresponding ylides which are then reacted with ketones to give substituted alkenamines, as described by Tretter et al. in U.S. Pat. No. 3,354,155 (1967). Thus stepwise treatment of (3-bromopropyl) triphenylphosphonium bromide with methylamine, n-butyllithium, and phthaloyl protected 3-aminoacetophenone (Aldrich Chemical Company) produces the phthaloyl protected N-methyl-4-(3-aminophenyl)-3-penten-1-amine. Removal of the phthaloyl protecting group using hydrazine hydrate will produce N-methyl-4-(3-aminophenyl)-3-penten-1-amine. In general, mixtures of E and Z isomers generated by such Wittig reactions are separable by chromatographic methods.

Another method by which branched olefinic compounds (i.e., those with alkyl or aryl substitution on one or both of the olefinic carbons) can be made is by the reaction of aryllithiums with various aminoketones, protected when necessary as their N-tert-butoxycarbonyl derivatives. The required protected aminoketones are produced from the commercially available haloketones by sequential process involving (i) reaction of a haloketone with ethylene glycol and p-toluenesulfonic acid (to produce the ethylene ketal), (ii) reaction of the haloketone ethylene ketal with a primary or secondary amine in N,N-dimethylformamide (to convert the halides into their corresponding secondary and tertiary amines), (iii) protection of the amino functionality by treatment with di-tert-butyl dicarbonate (to convert secondary amines into their N-tert-butoxycarbonyl derivatives), and (iv) treatment with pyridinium p-toluenesulfonate in acetone (to remove the ketal protecting group from the ketone). Alternatively the ethylene ketal can be removed by any of a variety of methods designed to retain other functionality, such as that described by Huet et al., *Synthesis* 63 (1978). Thus, 5-chloro-2-pentanone (Aldrich Chemical Company) and methylamine can be converted by the above reaction sequence into N-methyl-N-(tert-butoxycarbonyl)-5-amino-2-pentanone. Subsequent reaction of this protected aminoketone with a lithiated N-protected aniline, such as those described by Guijarro et al., *Tetrahedron* 49: 469–82 (1992) and by Gross et al., *J. Org. Chem.* 58: 2104–9 (1993), will afford an alcohol which can be converted to the alkene (mixture of E and Z isomers). Deprotection gives a mixture of E and Z isomers of N-methyl-4-(3-aminophenyl)-3-penten-1-amine.

The manner in which certain aryl substituted aliphatic amine compounds are synthetically produced can vary. Preparation of various aryl substituted aliphatic amine compounds can be carried out using the types of techniques similar to those disclosed by L. Rondahl, *Acta Pharm. Suec.* 13: 229–234 (1976). For example, an N-methyl-4-(3-aminophenyl)-3-butan-1-amine type compound can be prepared by the reaction of methylamine with the chloro-intermediate, 1-chloro4-(3-aminophenyl)-butane (or its hydrochloride salt). The latter compound can be obtained by treating 4-(3-aminophenyl)-butan-1-ol with thionyl chloride. The aliphatic alcohol, 4-(3-aminophenyl)-butan-1-ol can be prepared from the Heck reaction of 3-bromoaniline and 3-buten-1-ol, followed by hydrogenation of the olefinic intermediate, 4-(3-aminophenyl)-3-buten-1-ol. In another apporach, certain aryl substituted aliphatic amine compounds that possess a saturated side chain rather than an unsaturated side chain can be prepared by hydrogenation of the corresponding aryl substituted olefinic amine compounds or the corresponding acetylenic precursors. Hydrogenation procedures similar to those described by Kamimura et al., *Agr. Biol. Chem.* 27 (10): 684–688 (1963) can be used.

The manner in which certain aryl substituted olefinic amine compounds, such as (E)-N-methyl-5-(3-methoxyphenyl)-4-penten-2-amine, are provided can vary. By using one synthetic approach, the compound can be synthesized in a convergent manner, in which either 3-bromoanisole or 3-iodoanisole (commercially available from Aldrich Chemical Company or Lancaster Synthesis, Inc.) is coupled with the previously described side chain compound, N-methyl-N-(tert-butoxycarbonyl)-4-penten-2-amine under Heck reaction conditions, followed by removal of the tert-butoxycarbonyl protecting group with a strong acid such as trifluoroacetic acid. In a similar manner, (E)-N-methyl-4-(3-methoxyphenyl)-3-buten-1-amine can be prepared by the Heck coupling reaction of a 3-halo-anisole with the previously mentioned side chain compound, N-methyl-N-(tert-butoxycarbonyl)-3-buten-1-amine, followed by removal of the tert-butoxycarbonyl protecting group with a strong acid such as trifluoroacetic acid.

Certain commercially available fused polycyclic haloaromatics can be used to make the corresponding olefinic amine compounds using the previously described Heck reaction. Thus 6-bromoindole, commercially available from Biosynth Biochemica and Synthetica and protected on the ring nitrogen if necessary, can be coupled under palladium catalysis with 3-buten-1-ol using the procedures set forth in W. C. Frank et al., *J. Org. Chem.* 43: 2947 (1978) and N. J. Malek et al., *J. Org. Chem.* 47: 5395 (1982); the resulting alcohol intermediate allowed to react with p-toluenesulfonyl chloride to give the corresponding p-toluenesulfonate ester; and the ester treated with methylamine to give (E)-N-methyl-4-(6-indolyl)-3-buten-1-amine. The same compound can be produced by palladium catalyzed coupling of 6-bromoindole to N-methyl-N-(tert-butoxycarbonyl)-3-buten-1-amine (the synthesis of which is described above) and subsequently removing the tert-butoxycarbonyl protecting group. Alternatively, the 6-bromoindole can be reduced using diborane and trifluoroacetic acid in tetrahydrofuran as described by Gu et al., *Zhongguo Yaowu Huaxue Zazhi* 3: 58–9, 64 (1993) to give the corresponding 6-bromoindoline (6-bromo-2,3-dihydroindole), and the indoline protected as its tert-butoxycarbonyl derivative and used in the Heck coupling. Subsequent transformation as above and removal of the protecting group will yield (E)-N-methyl-4-(6-indolinyl)-3-buten-1-amine. Certain polycyclic phenols can also be converted into olefinic amines by first reacting them with trifluoromethanesulfonic anhydride to give the corresponding trifluoromethanesulfonate ester and subsequent palladium catalyzed coupling of the ester with a protected amine, as described by Sonesson et al., *J. Org. Chem.* 61: 4756 (1996), and further transformation as described above. Thus 8-hydroxyjulolidine, available from Aldrich Chemical Company, can be converted into (E)-N-methyl-4-(8-julolidinyl)-3-buten-1-amine.

Other polycyclic haloaromatics are available through well-known transformations of commercially available materials. Thus 1,3-benzodioxole (from Aldrich Chemical Company) can be nitrated to give 4-nitro-1,3-benzodioxole using the procedure described by Takakis et al., *J. Heterocycl. Chem.* 28: 625 (1991). Subsequent bromination, as taught by Dauksas et al., *Khim. Geterotsikl. Soedin.* Issue 9: 1183 (1979) gives 6-bromo-4-nitro-1,3-benzodioxole. Reduction of the nitro group to the amine group, accomplished with either tin or iron filings in hydrochloric acid, provides 4-amino-6-bromo-1,3-benzodioxole which can be coupled in a Heck process, as previously described, to give (E)-N-methyl-4-(6-(4-amino-1,3-benzodioxol)yl)-3-buten-1-amine.

In a similar application, 4-bromo-2-nitrophenol (available from Aldrich Chemical Company) and 4-bromo-2-nitroaniline (available from Trans World Chemicals, Inc.) can be reduced to 2-amino-4-bromophenol and 4-bromo-1,2-diaminobenzene respectively using tin and hydrochloric acid. Alternatively, stannous chloride can be used as the reducing agent, as described by Manjarrez et al., *Rev. Soc. Quim. Mex.* 30: 52 (1986). Reaction of 2-amino-4-bromophenol with trimethyl orthoformate in methanol provides 5-bromobenzoxazole, as reported by Kunz et al., *Org. Prep. Proced. Int.* 22: 613 (1990). Similarly, condensation of 4-bromo-1,2-diaminobenzene with formic acid in the presence of 6 M hydrochloric acid gives 5(6)-bromobenzimidazole, as described by Goldsmith et al. in U.S. Pat. No. 3,325,271. 5(6)-Bromobenzimidazole can also be made by brominating the commercially available benzimidazole (Aldrich Chemical Company) with bromine in aqueous ammonia according to Popov et al. in Soviet Union Patent No. 1,616,912. Applying the previously described Heck chemistry to 5-bromobenzoxazole and 5(6)-bromobenzimidazole will produce (E)-N-methyl-4-(5-benzoxazolyl)-3-buten-1-amine and (E)-N-methyl-4-(5(6)-benzimidazolyl)-3-buten-1-amine, respectively. In another application of this chemistry, 4-bromo-1,2-diaminobenzene can be condensed with glyoxal hydrate to give 6-bromoquinoxaline, which can subsequently be converted into (E)-N-methyl-4-(6-quinoxalinyl)-3-buten-1-amine. In yet another application, 2-amino-4-bromophenol can be converted into 6-bromobenzoxazine by the action of 1,2-dihaloethane as described by Benoit et al., *J. Pharm. Chim.* 22: 544 (1935). Thus produced, the 6-bromobenzoxazine can be protected as its N-tert-butoxycarbonyl derivative and submitted to Heck coupling and removal of the protecting group to give (E)-N-methyl-4-(6-benzoxazinyl)-3-buten-1-amine. Furthermore, acetylation of 4-bromo-1,2-diaminobenzene with acetic anhydride followed by treatment with thallium (III) trifluoroacetate in trifluoroacetic acid, as described by Lau et al., *Tetrahedron Lett.* 22: 1175 (1981), gives 4-acetamido-6-bromo-2-methylbenzoxazole which can be converted into (E)-N-methyl-4-(6-(4-acetamido-2-methylbenzoxazol)yl)-3-buten-1-amine using the Heck coupling.

Certain 4-amino-6-halobenzofurans, which are starting materials for the Heck reaction, are readily accessible by elaboration of the previously described 3-halo-5-methoxyanilines, synthesized as described by Emokpae et al., *J. Chem. Soc., Perkin Trans.* 2(1): 14 (1977) and Liedholm, *Acta Chem. Scand., Ser. B*, 38: 877 (1984). Thus, 3-bromo-5-methoxyaniline can be demethylated with hydrobromic acid to give 3-amino-5-bromophenol. Protection of the amino group as its phthaloyl derivative and alkylation of the phenolic oxygen with allyl bromide and potassium carbonate will provide the allyl phenyl ether. This latter material (either as the free amine or the protected amine) can be induced to undergo Claisen rearrangement and ring closure to the corresponding 2,3-dihydro-2-methylbenzofuran by a variety of well established chemistries, such as that of Kim et al., *Heterocycles* 36: 497 (1993) and those reviewed by Lutz, *Chem. Rev.* 84: 205 (1984). The 4-amino-6-bromo-2,3-dihydro-2-methylbenzofuran, thus produced, can be converted into the target (E)-N-methyl-4-(6-(4-amino-2,3-dihydro-2-methylbenzofuran)yl)-3-buten-1-amine by the palladium catalyzed coupling reactions and associated chemistry described earlier. This approach to the synthesis of benzofuran-containing alkenyl amines is general in the sense that a variety of allylic halides can be used to alkylate the phenol, thus producing, after Claisen rearrangement and ring closure, a variety of alkyl substituted 2,3-dihydrobenzofurans and 3,4-dihydrobenzopyrans.

Aryl substituted aliphatic amine compounds that possess a cyclopropyl moiety in the side chain can be prepared by a variety of methods. In one synthetic approach, aryl substituted cyclopropyl analogs can be prepared from the aforementioned aryl substituted olefinic amine compounds. Aryl substituted olefinic amine compounds possessing either an (E) or (Z) geometry can be converted to the corresponding trans and cis cyclopropane derivatives, respectively by treatment of the olefinic compounds with methylene iodide and a zinc-copper couple using the types of procedures set forth in H. E. Simmons et al., *J. Amer. Chem. Soc.* 81: 4256–4264 (1959). In particular, compounds such as (E)-4-(3-aminophenyl)-3-buten-1-amine, (E)-N-methyl-4-(3-aminophenyl)-3-buten-1-amine, (E)-N-methyl-5-(3-aminophenyl)-4-penten-2-amine, and (E)-N-methyl-5-(3-methoxyphenyl)-4-penten-2-amine can be converted to their corresponding cyclopropyl derivatives using the Simmons-Smith procedure.

Certain compounds that possess an arylmethyl ether skeleton, such as an N-methyl-2-[(3-aminophenyl)methoxy]-ethan-1-amine type compound, can be prepared by a number of methods. In one approach, a 3-aminobenzyl alcohol type compound (N-protected as the phthalimide) can be condensed with the p-toluenesulfonate ester of ethanolamine, possessing a protected amine functionality, namely 2-p-toluenesulfonyloxy-[N-methyl-N-(tert-butoxycarbonyl)]-ethan-1-amine. Typically a strong base such as sodium hydride and an aprotic dipolar solvent such as N,N-dimethylformamide are used for the condensation. The tert-butoxycarbonyl protecting group of the resulting arylmethyl ether type compound can be removed with trifluoroacetic acid, followed by removal of the phthaloyl group with methylamine or hydrazine affording N-methyl-2-[(3-aminophenyl)methoxy]-ethan-1-amine. Substituted benzyl alcohol starting materials such as 3-aminobenzyl alcohol are commercially available from Aldrich Chemical Company. The phthalimide of 3-aminobenzyl alcohol can be prepared by heating 3-aminobenzyl alcohol with phthlic anhydride under reflux with azeotropic removal of water according to the method of J. F. Bunnett et al., *J. Org. Chem.* 27: 3836–3843 (1962). Protected amino side chain compounds such as 2-p-toluenesulfonyloxy-[N-methyl-N-(tert-butoxycarbonyl)]-ethan-1-amine can be prepared using the methods set forth in J. Christoffers, *Liebigs Ann./Recl.* (7): 1353–1358 (1997). By using this synthetic approach, substituted benzyl alcohol starting materials such as 4-methyl-3-nitrobenzyl alcohol, 4-chloro-3-nitrobenzyl alcohol, 3-nitrobenzyl alcohol, and 3,4-dimethoxybenzyl alcohol (commercially available from Acros Organics) can be elaborated to give N-methyl-2-[(4-methyl-3-nitrophenyl)methoxy]-ethan-1-amine, N-methyl-2-[(4-chloro-3-nitrophenyl)methoxy]-ethan-1-amine, N-methyl-2-[(3-nitrophenyl)methoxy]-ethan-1-amine, and N-methyl-2-[(3,4-dimethoxyphenyl)methoxy]-ethan-1-amine, respectively.

Compounds with an arylmethyl ether functionality and which also possess a branched side chain, such as an N-methyl-1-[(3-aminophenyl)methoxy]-propan-2-amine type compound, can be prepared by a number of methods. In one approach, a 3-aminobenzyl alcohol type compound (N-protected as the phthalimide) can be alkylated with 1-bromo-2-propanol type compound containing an O-protecting group, such as 2-(2-bromo-1-methylethoxy) tetrahydro-2H-pyran. Typically a strong base such as sodium hydride and a solvent such as N,N-dimethylformamide or tetrahydrofuran are used for the alkylation. The tetrahydropyranyl protecting group of the resulting arylmethyl ether type compound can be removed with aqueous sulfuric acid in methanol, affording 1-[(3-aminophenyl)methoxy]-propan-2-ol. The latter alcohol can be elaborated to the corresponding methylamino compound by conversion to its p-toluenesulfonate ester by treatment with p-toluenesulfonyl chloride, followed by tosylate displacement with methylamine and finally removal of the N-phthaloyl group affording N-methyl-1-[(3-aminophenyl)methoxy]-propan-2-amine. Side chain compounds such as 2-(2-bromo-1-methylethoxy)tetrahydro-2H-pyran can be prepared from 1-bromo-2-propanol (commercially available from Aldrich Chemical Company) by treatment with 2,3-dihydropyran in dichloromethane with p-toluenesulfonic acid as a catalyst according to the methods of S. A. M. Nieuwenhuis et al., *Tetrahedron* 50: 13207–13230 (1994).

The manner in which optically active forms of arylmethoxy aliphatic amines, such as (2S)-N-methyl-1-[(3-aminophenyl)methoxy]-propan-2-amine type compounds, are provided can vary. In one approach, a 3-aminobenzyl alcohol type compound (N-protected as the phthalimide) can be alkylated with a chiral 1-bromo-2-propanol type compound containing an O-protecting group, such as (1S)-2-(2-bromo-1-methylethoxy)tetrahydro-2H-pyran using a base such as sodium hydride and a solvent such as N,N-dimethylformamide or tetrahydrofuran. The tetrahydropyranyl protecting group of the resulting chiral arylmethyl ether type compound can be removed with aqueous sulfuric acid in methanol, affording (2S)-1-[(3-aminophenyl)methoxy]-propan-2-ol. The resulting chiral alcohol intermediate can be converted to its corresponding tosylate, followed by tosylate displacement with methylamine with inversion of configuration, and finally removal of the N-phthaloyl group to give the chiral amine (2R)-N-methyl-1-[(3-aminophenyl) methoxy]-propan-2-amine. Chiral side chain compounds such as (1S)-2-(2-bromo-1-methylethoxy)tetrahydro-2H-pyran can be prepared from (2S)-1-bromo-2-propanol by treatment with 3,4-dihydro-2H-pyran in dichloromethane with p-toluenesulfonic acid as a catalyst according to the method of S. A. M. Nieuwenhuis et al., *Tetrahedron* 50: 13207–13230 (1994). The required (2S)-1-bromo-2-propanol can be obtained from (S)-propylene oxide (commercially available from Fluka) by treatment with hydrogen bromide in acetic acid at 0° C. The corresponding optical antipode, (2R)-N-methyl-1-[(3-aminophenyl) methoxy]-propan-2-amine can be prepared in an analogous manner from (R)-propylene oxide (commercially available from Fluka) by using the synthetic procedure of S. A. M. Nieuwenhuis et al. to prepare the tetrahydropyranyl ether of (2R)-1-bromo-2-propanol and by using the synthetic sequence described above.

Alternatively, the same chiral side-chain can be derived from N-methyl-L-alanine and N-methyl-D-alanine (available from Sigma) by reduction with lithium aluminum hydride to give the corresponding N-methylaminopropanols, and subsequent reaction with di-tert-butyl dicarbonate (to protect the amino group) and p-toluenesulfonyl chloride (to esterify the alcohol). These transformations are similar to those reported by Schessinger et al., *Tetrahedron Lett.* 28: 2083–2086 (1987). The (S) and (R) 1-p-toluenesulfonyloxy-N-methyl-N-(tert-butoxycarbonyl)-2-propanamines which result can be used to alkylate phthaloyl protected 3-aminobenzyl alcohols in the same manner as described above for 2-p-toluenesulfonyloxy-N-methyl-N-(tert-butoxycarbonyl)-1-ethanamine.

Other 3-aminobenzyl alcohols are provided by well-known transformations of commercially available materials. Thus 3-aminoacetophenone, from Aldrich Chemical Company, can be reduced to racemic 3-amino-α-methylbenzyl alcohol by sodium borohydride in the presence of acetic acid as described by Nieminen et al., *Tetrahedron Lett.* 28: 4725–8 (1987). Alternatively, the phthaloyl protected 3-aminoacetophenone can be reduced with either of the enantiomers of B-chlorodiisopino-campheylborane (DIP-chloride, Aldrich Chemical Company) to produce the protected, enantiomerically pure 3-amino-α-methylbenzyl alcohol according to the procedures reported by Brown et al., *Acc. Chem. Res.* 25: 16 (1992). Other α-mono-substituted 3-aminobenzyl alcohols can be accessed by addition of the appropriate alkyl- or aryllithium or alkyl- or arylmagnesium halide reagent to the phthaloyl protected 3-aminobenzaldehyde, which can be made from commercially available 3-nitrobenzaldehyde (Aldrich Chemical Company). Thus, treatment of 3-nitrobenzaldehyde with ethylene glycol and p-toluenesulfonic acid produces the ethylene acetal. The nitro group can then be reduced with sodium borohydride to the amino group, which can be protected as its phthaloyl derivative. Hydrolysis of the ethylene acetal with aqueous acetic acid gives phthaloyl protected 3-aminobenzaldehyde. Addition of n-butyllithium to phthaloyl protected 3-aminobenzaldehyde yields the phthaloyl derivative of 1-(3-aminophenyl)-1-pentanol. Similarly di-substitution (methyl and alkyl or aryl) on the α-carbon of the benzyl alcohol can be accomplished by treatment of the phthaloyl protected 3-aminoacetophenone with alkyl- or aryllithium or alkyl- or arylmagnesium halide reagents. Alternatively, a variety of α-mono-substituted and α,α-di-substituted 3-aminobenzyl alcohols are available by the method of Guijarro et al., *Tetrahedron* 49: 469–82 (1993). Thus, 3-chloroaniline (Aldrich Chemical Company) is converted into its pivaloyl derivative and then treated sequentially with n-butyllithium, lithium metal in the presence of catalytic amount of naphthalene, and an aldehyde or ketone to produce the pivaloyl derivatives of α-mono-substituted and α,α-di-substituted 3-aminobenzyl alcohols, respectively. Thus, when this process is carried out using cyclohexanone as the carbonyl component, the 1-(N-pivaloyl-3-aminophenyl)cyclohexanol is the product. In a similar process, reported by Gross et al., *J. Org. Chem.* 58: 2104–9 (1993), 3-bromoaniline is converted to its 3,3-(1,4-butanediyl)triazene derivative by diazotization and reaction with pyrrolidine. The 3-bromophenyltriazene can then be converted, by treatment with sec-butyllithium, into the 3-lithiophenyltriazene, which can then be reacted with carbonyl electrophiles to give triazene protected α-mono-substituted and α,α-di-substituted 3-aminobenzyl alcohols. Reaction of the protected (phthaloyl, pivaloyl, or triazene derivatives) 3-aminobenzyl alcohols (with or without (α-substitution) with sodium hydride and either 2-p-toluenesulfonyloxy-1-(N-methyl-N-(tert-butoxycarbonyl)) ethanamine or 1-p-toluenesulfonyloxy-2-(N-methyl-N-(tert-butoxycarbonyl)propanamine (the synthesis of which is described above), will provide, after removal of the protecting groups, the corresponding N-methyl-2-(3-aminophenyl) methoxy-1-ethanamines and N-methyl-1-(3-aminophenyl) methoxy-2-propanamines with or without substitution α to the aniline ring. The amine protecting groups used in these ether syntheses can be removed by the following means: phthaloyl (hydrazine hydrate in methanol); pivaloyl (lithium aluminum hydride); 3,3-(1,4-butanediyl)triazene (nickel-aluminum alloy in methanolic potassium hydroxide); tert-butoxycarbonyl (trifluoroacetic acid). Thus, the reaction of phthaloyl protected 3-amino-α-methylbenzyl alcohol with sodium hydride and 1-p-toluenesulfonyloxy-2-(N-methyl-N-(tert-butoxycarbonyl))propanamine, and subsequent treatment with hydrazine hydrate (to remove the phthaloyl group) and then trifluoroacetic acid (to remove the tert-butoxycarbonyl group), will provide N-methyl-1-(1-(3-aminophenyl)ethoxy)-2-propanamine. Either enantiomer of either component may be used or the racemate of one component can be condensed with a single enantiomer of the other to give diasteriomeric amines, which are potentially separable by chromatographic methods. In another application of this chemistry, the triazene derivative of 1-(3-aminophenyl)cyclohexanol can be reacted with sodium hydride and 2-p-toluenesulfonyloxy-1-(N-methyl-N-(tert-butoxycarbonyl)ethanamine, and subsequently treated with nickel-aluminum alloy in methanolic potassium hydroxide (to convert the triazene to the amino group) and then trifluoroacetic acid, producing N-methyl-2-(1-(3-aminophenyl)cyclohexyloxy)-1-ethanamine.

Aromatic ring-substituted 3-aminobenzyl alcohols can also be used to produce compounds of the present invention. The means by which such ring-substituted 3-aminobenzyl alcohols are produced can vary. One method consists of reacting a substituted N-protected 3-haloaniline with n-butyllithium or sec-butyllithium followed by a formaldehyde equivalent (like paraformaldehyde), as described by Guijarro et al., *Tetrahedron* 49: 469–82 (1993) and Gross et al., *J. Org. Chem.* 58: 2104–9 (1993). Using this technology, the various ring-substituted bromoanilines and fused ring aryl bromides described earlier (as useful in the Heck coupling) are potential starting materials for production of the corresponding benzyl alcohols. Thus, 3-bromo-5-methoxyaniline (synthesized as described by Emokpae et al., *J. Chem. Soc., Perkin Trans.* 2(1): 14–17 (1977)) can be converted into its triazene derivative, lithiated, and reacted with paraformaldehyde (as described by Gross et al., *J. Org. Chem.* 58: 2104–9 (1993)). The resulting triazene protected 3-amino-5-methoxybenzyl alcohol can be reacted with sodium hydride and 2-p-toluenesulfonyloxy-N-methyl-N-(tert-butoxycarbonyl)-1-ethanamine. Removal of the protecting groups (as previously described) then affords N-methyl-2-(3-amino-5-methoxyphenyl)methoxy-1-ethanamine.

Certain other ring-substituted and fused-ring benzyl alcohols are readily prepared from the corresponding aldehydes and carboxylic acids by reduction with a hydride reducing agent. For example, M. Bianchi et al., *Chim. Ind.* 49: 392 (1967) described the conversion of 3-amino-4-hydroxybenzoic acid (Aldrich Chemical Company) into its formamide by refluxing formic acid and the subsequent heating of the formamide to produce 5-benzoxazolecarboxylic acid. Treatment of the acid with thionyl chloride produces the corresponding acid chloride which can then be reduced to 5-(hydroxymethyl) benzoxazole. This s fused-ring benzyl alcohol can be condensed with 1-p-toluenesulfonyloxy-N-methyl-N-(tert-butoxycarbonyl)-2-propanamine using sodium hydride to give, after deprotection, N-methyl-1-(5-benzoxazolyl) methoxy-2-propanamine. In another similar case, piperonylic acid (Aldrich Chemical Company) can be nitrated to give 5-nitropiperonylic acid (5-nitro-3,4-methylenedioxybenzoic acid), which can subsequently be reduced to 5-aminopiperonyl alcohol (5-amino-3,4-methylenedioxybenzyl alcohol) by sequential treatment with tin in hydrochloric acid and lithium aluminum hydride. Protection of this amine as its phthaloyl derivative, followed by reaction with sodium hydride and 2-p-toluenesulfonyloxy-N-methyl-N-(tert-butoxycarbonyl)-1-ethanamine results in formation of the benzyl ether compound. Subsequent removal of the protecting groups, affords N-methyl-2-(5-amino-3,4-methylenedioxyphenyl)methoxy-1-ethanamine.

Compounds that possess an arylmethyl ether functionality with a cyclic amine fragment, such as a 3-((2-pyrrolidinylethoxy)methyl)phenylamine type compound can be prepared by a variety of methods. By one synthetic approach, the p-toluenesulfonate ester of a 3-aminobenzyl alcohol type compound (N-protected as the phthalimide) can be used to alkylate 1-(2-hydroxyethyl)pyrrolidine (commercially available from Aldrich Chemical Company) in the presence of a base such as sodium hydride in a solvent such as tetrahydrofuran or N,N-dimethylformamide. The phthaloyl protecting group of the resulting intermediate can be removed by treatment with methylamine or hydrazine yielding the 3-((2-pyrrolidinylethoxy)methyl)phenylamine.

Compounds that possess an arylmethyl ether functionality with a chiral azacyclic fragment, such as 3-((pyrrolidin-2(S)-ylmethoxy)methyl)phenylamine and 3-(((1-methylpyrrolidin-2(S)-yl)methoxy)methyl)phenylamine type compounds can be prepared by a number of methods. By one synthetic approach, the p-toluenesulfonate ester of a 3-aminobenzyl alcohol type compound (N-protected as the phthalimide) can be used to alkylate (S)-1-(tert-butoxycarbonyl)-2-pyrrolidinemethanol in the presence of a base such as sodium hydride in a solvent such as tetrahydrofuran or N,N-dimethylformamide. The tert-butoxycarbonyl group can be removed with strong acid such as trifluoroacetic acid or hydrochloric acid and the phthaloyl group can be removed by treatment with hydrazine or methylamine producing 3-((pyrrolidin-2(S)-ylmethoxy) methyl)phenylamine. The required (S)-1-(tert-butoxycarbonyl)-2-pyrrolidinemethanol is commercially available from Aldrich Chemical Company. The corresponding enantiomer, 3-((pyrrolidin-2(R)-ylmethoxy)methyl)-phenylamine can be prepared in an analogous manner from (R)-1-(tert-butoxycarbonyl)-2-pyrrolidinemethanol (commercially available from Aldrich Chemical Company). It should be mentioned that (S)-1-(tert-butoxycarbonyl)-2-pyrrolidinemethanol and (R)-1-(tert-butoxycarbonyl)-2-pyrrolidinemethanol can be prepared according to the methods of D. A. Evans et al., *J. Am. Chem. Soc.* 101: 371–378 (1979) and B. D. Harris et al., *Heterocycles* 24: 1045–1060 (1986) starting from commercially available (Aldrich Chemical Company) D-proline and L-proline. Compounds of the present invention such as 3-(((1-methylpyrrolidin-2(S)-yl)methoxy)methyl)phenylamine can be prepared in a similar manner by the alkylation of (S)-1-methyl-2-pyrrolidinemethanol (available from Aldrich Chemical Company) with the previously mentioned p-toluenesulfonate ester of a 3-aminobenzyl alcohol (N-protected as the phthalimide), followed by removal of the tert-butoxycarbonyl and phthaloyl protecting groups. The corresponding enatiomer of the above N-methyl compound, namely 3-(((1-methylpyrrolidin-2(R)-yl) methoxy)methyl)phenylamine can be prepared in a similar manner by the alkylation of (R)-1-methyl-2-pyrrolidinemethanol with the previously mentioned p-toluenesulfonate ester of a 3-aminobenzyl alcohol (N-protected as the phthalimide), followed by removal of the tert-butoxycarbonyl and phthaloyl protecting groups. The required (R)-1-methyl-2-pyrrolidinemethanol can be prepared by the method of R. E. Gawley et al., *J. Org. Chem.* 60 (18): 5763–5769 (1995).

Compounds that possess an arylmethyl ether functionality with a chiral azacyclic fragment, such as 3-((2(S)-azetidinylmethoxy)methyl)phenylamine and 3-(((1-methyl-2(S)-azetidinyl)-methoxy)methyl)phenylamine type compounds can be prepared by a variety of synthetic methods. In one synthetic approach, the p-toluenesulfonate ester of a 3-aminobenzyl alcohol type compound (N-protected as the phthalimide) can be used to alkylate (S)-1-(tert-butoxycarbonyl)-2-azetidinemethanol in the presence of a base such as sodium hydride in a solvent such as tetrahydrofuran or N,N-dimethylformamide. The tert-butoxycarbonyl group can be removed with a strong acid such as trifluoroacetic acid or hydrochloric acid and the phthaloyl group can be removed by treatment with hydrazine or methylamine affording 3-((2(S)-azetidinylmethoxy) methyl)phenylamine. The requisite nonracemic compound, (S)-1-tert-butoxycarbonyl)-2-azetidinemethanol can be prepared from (S)-2-azetidinecarboxylic acid (commercially available from Aldrich Chemical Company) using the method of M. A. Abreo et al., *J. Med. Chem.* 39: 817–825 (1996). The enantiomeric azetidinyl compound, 3-((2(R)-azetidinylmethoxy)-methyl)phenylamine can be prepared in an analogous way by coupling 3-aminobenzyl alcohol type compound (N-protected as the phthalimide) with (R)-1-(benzyloxycarbonyl)-2-azetidinemethanol, followed by treatment with base, such as methanolic potassium hydroxide to remove the benzyloxycarbonyl protecting group and treatment with hydrazine or methylamine to remove the phthaloyl protecting group. The required (R)-1-

(benzyloxycarbonyl)-2-azetidinemethanol can be prepared from D-methionine using the methodology of M. A. Abreo et al., *J. Med. Chem.* 39: 817–825 (1996). Compounds of the present invention such as 3-(((1-methyl-2(S)-azetidinyl)methoxy)methyl)phenylamine and its enantiomeric compound, 3-(((1-methyl-2(R)-azetidinyl)methoxy)methyl)phenylamine can be prepared by methylation of the previously described secondary amino compounds, 3-((2(S)-azetidinylmethoxy)methyl)phenylamine and 3-((2(R)-azetidinylmethoxy)methyl)phenylamine, respectively, each N-protected as the phthalimide. Methylation methods employing aqueous formaldehyde and sodium cyanoborohydride as described by M. A. Abreo et al., *J. Med. Chem.* 39: 817–825 (1996) can be used. Removal of the phthaloyl group can be accomplished under mild conditions using sodium borohydride in 2-propanol as described by J. O. Osby et al., *Tetrahedon Lett.* 25(20): 2093–2096 (1984).

Using this approach, other compounds containing arylmethyl ether and azacyclic functionality can be made. Thus, the commercially available 3-pyrrolidinol and 3-quinuclidinol (both from Aldrich Chemical Company) can be converted into their N-tert-butoxycarbonyl derivatives by reaction with di-tert-butyl dicarbonate. Subsequent alkylation with sodium hydride and the p-toluenesulfonate ester of phthaloyl protected 3-aminobenzyl alcohol in N,N-dimethylformamide, followed by removal of the protecting groups, will generate 3-(3-aminobenzyloxy)pyrrolidine and 3-(3-aminobenzyloxy)quinuclidine, respectively. Alternatively, the alkylation can be carried out with 3-nitrobenzyl bromide (Aldrich Chemical Company) to produce the corresponding 3-(3-nitrobenzyloxy)pyrrolidine and 3-(3-nitrobenzyloxy)quinuclidine.

Certain compounds may contain a thiazoline ring. The methods by which such thiazoline containing compounds can be synthesized can vary. One method involves the condensation of a thioamide or thiourea with an α-haloaldehyde, such as 2-chloroacetaldehyde or 2-bromoacetaldehyde. The requisite thioamides and thioureas can be produced in a number of ways. For instance, the alkoxide of 3-nitrobenzyl alcohol (Aldrich Chemical Company) can be converted to 3-chloro-1-((3-nitrophenyl)methoxy)propane by treatment with 3-chloro-1-iodopropane (Aldrich Chemical Company). Conversion of this compound to the corresponding amine can be accomplished by a variety of methods known in the art, such as by Gabriel synthesis (Gibson and Bradshaw, *Agnew. Chem. Int. Eng. Ed.* 7: 919 (1968)), whereby the alkyl chloride is converted to the phthalimide followed by removal of the phthaloyl protecting group with hydrazine. Then, the resulting 3-((3-nitrophenyl)methoxy)-1-propanamine can be converted into its thiourea by treatment with thiocyanic acid in DMF. This mono-substituted thiourea can then be cyclized to form N-(2-thiazolyl)-3-((3-nitrophenyl)methoxy)-1-propanamine using chloracetaldehyde (Aldrich Chemical Company) in the presence of magnesium sulfate as described by Bramley et al., *J. Chem. Soc. Perkin Trans. I* 13: 639 (1987). Finally, any number of methods known to the art of organic synthesis can be used to reduce the aryl nitro group to give the desired aryl amine, N-(2-thiazolyl)-3-((3-aminophenyl)methoxy)-1-propanamine. One such method is the use of hexarubidium-carbonyl and N,N,N, N-tetramethyl-1,3-propanediamine according to the method of Kiyotomi et al., *J. Mol. Catal.* 88: L267 (1994). Alternatively, the thiourea of 3-((3-nitrophenyl)methoxy)-1-propanamine can be cyclized to form 3-(3-((3-nitrophenyl)methoxy)propyl)-2,3-dihydrothiazolin-2-imine, using chloroacetaldehyde in the presence of hydrochloric acid as described by Bramley et al., *J. Chem. Soc. Perkin Trans. I* 13: 639 (1987). Reduction to the corresponding aryl amine can be accomplished as described above.

The present invention relates to a pharmaceutical composition incorporating a compound selected from the general formulae which are set forth hereinbefore. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. No. 5,597,919 to Dull et al., U.S. Pat. No. 5,861,423 to Caldwell et al., U.S. Pat. No. 5,811,442 to Bencherif et al., U.S. Pat. No. 5,726,316 to Crooks et al., U.S. Pat. No. 5,616,716 to Dull et al. and U.S. Pat. No. 5,663,356 to Ruecroft et al.

The present invention relates to a method for providing treatment of diseases and disorders associated with dysfunction associated with normal cytokine production and/or secretion (e.g., unregulated or excessive cytokine production and/or secretion). In particular, the present invention relates to a method for inhibiting cytokine production and/or secretion. Typically, compounds of the present invention are administered to a subject susceptible to such a condition or to a subject suffering from such as condition. In particular, the method comprises administering to a patient an amount of a compound effective for providing some degree of prevention of the progression of such a condition (i.e., provide protective effects), amelioration of the symptoms of the disorder, and/or amelioration of the reoccurence of the disorder. Typically, the method of the present invention comprises administering to a patient in need thereof, an amount of a compound of the present invention, which amount is effective to prevent or treat the condition affecting the patient. The present invention also relates to pharmaceutical compositions incorporating compounds of the present invention.

The pharmaceutical compositions of the present invention can be employed to prevent or treat a wide variety of conditions, diseases and disorders. Exemplary diseases and disorders include inflammatory bowel disease, acute cholangitis, aphteous stomatitis, arthritis (e.g., rheumatoid arthritis and ostearthritis), neurodegenerative diseases, cachexia secondary to infection (e.g., as occurs in AIDS, AIDS related complex and neoplasia), as well as those indications set forth in PCT WO 98/25619. The pharmaceutical compositions of the present invention can be employed in order to ameliorate may of the symptoms associated with those conditions, diseases and disorders. Thus, pharmaceutical compositions of the present invention can be used in treating genetic diseases and disorders, in treating autoimmune disorders such as lupus, as anti-infectious agents (e.g, for treating bacterial, fungal and viral infections, as well as the effects of other types of toxins such as sepsis), as anti-inflammatory agents (e.g., for treating acute cholangitis, aphteous stomatitis, asthma, and ulcerative colitis), and as inhibitors of cytokines release (e.g., as is desirable in the treatment of cachexia, inflammation, neurodegenerative diseases, viral infection, and neoplasia), The compound of the present invention can also be used as adjunct therapy in combination with existing therapies in the management of the aforementioned types of diseases and disorders.

The pharmaceutical composition also can include various other components as additives or adjuncts. Exemplary pharmaceutically acceptable components or adjuncts include antioxidants, free radical scavenging agents, peptides, antibiotics, bacteriostatic agents, immunosuppressives, buffering agents, anti-inflammatory agents, anti-pyretics, analgesics, anti-diarrheal agents, membrane stabilizing agents, oils, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); as a suppository or an enema; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet (e.g., as is Asacol), a hard gelatin capsule (e.g., as is Dipentum) or as a rectal suspension enema (e.g., as is Rowasa). As another example, the compounds can be delivered transdermally using the types of patch technologies available from Ciba-Geigy Corporation and Alza Corporation. The administration of the pharmaceutical compositions of the present invention can be intermittent, or at a gradual, continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation act to optimize effects upon abnormal cytokine production, while minimizing effects upon receptor subtypes such as those that are associated with muscle and ganglia. Administration preferably is such that active ingredients interact with regions where cytokine production is affected or occurs.

The appropriate dose of the compound is that amount effective to prevent occurrence of the symptoms of the condition or to treat some symptoms of the condition from which the patient suffers. By "effective amount", "therapeutic amount" or "effective dose" is meant that amount sufficient to elicit the desired pharmacological or therapeutic effects, thus resulting in effective prevention or treatment of the condition. Prevention of the condition is manifested by a prolonging or delaying of the onset of the symptoms of that condition. Treatment of the condition is manifested by a decrease in the symptoms associated with the condition or an amelioration of the reoccurrence of the symptoms of the condition.

The effective dose can vary, depending upon factors such as the condition of the patient, the severity of the symptoms of the disease or disorder, and the manner in which the pharmaceutical composition is administered. Compounds of the present invention are very potent (i.e., affect cytokine production and/or secretion at very low concentrations), and are very efficacious (i.e., significantly inhibit cytokine production and/or secretion to a relatively high degree). Effective doses are most preferably at very low concentrations, where maximal effects are observed to occur. Concentrations, determined as the amount of compound per volume of relevant tissue, typically provide a measure of the degree to which that compound affects cytokine production. For human patients, the effective dose of typical compounds generally requires administering the compound in an amount of at least about 1, often at least about 10, and frequently at least about 25 ug/24 hr./patient. For human patients, the effective dose of typical compounds requires administering the compound which generally does not exceed about 1, often does not exceed about 0.75, often does not exceed about 0.5, frequently does not exceed about 0.25 mg/24 hr./patient. In addition, administration of the effective dose is such that the concentration of the compound within the plasma of the patient normally does not exceed 500 pg/ml, often does not exceed 300 pg/ml, and frequently does not exceed 100 pg/ml. Compounds of the present invention are dose dependent, and as such, cause inhibition of cytokine production and/or secretion when employed at low concentrations but do not exhibit those inhibiting effects at higher concentrations. Compounds of the present invention exhibit inhibitory effects upon cytokine production and/or secretion when employed in amounts less than those amounts necessary to elicit activation of relevant nicotinic receptor subtypes to any significant degree.

The compounds of the present invention, when employed in effective amounts in accordance with the method of the present invention, are selective to certain relevant nicotinic receptors, but do not cause significant activation of receptors associated with unwanted side effects. By this is meant that a particular dose of compound resulting in prevention and/or treatment effects resulting from undesirable levels of cytokine production is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland.

The compounds of the present invention, when employed in effective amounts in accordance with the method of the present invention, also lack the ability to elicit activation of nicotinic receptors of human muscle to any significant degree. In that regard, the compounds of the present invention demonstrate poor ability to cause isotopic rubidium ion flux through nicotinic receptors in cell preparations derived from muscle preparations. Thus, such compounds exhibit receptor activation constants (i.e., which provide a measure of the concentration of compound needed to activate half of the relevant receptor sites of the skeletal muscle of a patient) which are relatively high.

Compounds of the present invention, when employed in effective amounts in accordance with the method of the present invention, are effective towards providing some degree of inhibition of cytokine production. However, such effective amounts of those compounds are not sufficient to elicit any appreciable side effects, such as those demonstrated by increased effects relating to the cardiovascular system, and effects to skeletal muscle. As such, administration of compounds of the present invention provides a therapeutic window in which cytokine inhibition is provided, and side effects are avoided. That is, an effective dose of a compound of the present invention is sufficient to provide the desired effects, but is insufficient (i.e., is not at a high enough level) to provide certain undesirable side effects. Typically, effective administration of a compound of the present invention resulting in cytokine inhibition occurs upon administration of much less that amount sufficient to cause such side effects to a significant degree.

The following example is provided in order to further illustrate various embodiments of the invention but should not be construed as limiting the scope thereof. Unless otherwise noted, all parts and percentages are by weight.

EXAMPLE

Cytokine Inhibition

Human acute monocytic leucaemia cells (MonoMac 6 cells) and human erythroleukemia bone marrow cells (TF-1 cells) were obtained by CellControl GmbH. Each cell type was individually suspended in culture medium. The culture medium was composed of RPMI, 10% FCS, and 50 uM mercaptoethanol. Each mixture of cells and culture medium then were seeded on polycarbonate membranes at a density of about 500,000 cells per cell cup. A compound of the present invention then was added to the cell and culture medium mixture, and the mixtures then were incubated for 15 hours at 37° C. and 5% carbon dioxide. Then, each mixture was stimulated with lipopolysaccharid (LPS) at a concentration of 1 ng/ml. The metabolic activation of the cells was measured using a macrophyio-meter to measure the extracellular acidification rates. See, Metzger et al., BioTec, 1 (1993) and McConnell et al., Science, 257: 1906–1912 (1992).

Sample No. 1 is (Z)-metanicotine monofumarate, and the manner of synthesis for that compound is set forth in U.S. Pat. No. 5,604,231 to Smith et al. The EC50 is 100 nM, and the Emax is 100 percent.

Sample No. 2 is of (E)-4-[3-(5-methoxypyridin)yl]-3-buten-1-amine monofumarate, and the manner of synthesis for that compound is set forth in U.S. Pat. No. 5,604,231 to Smith et al. The EC50 is 0.2 nM, and the Emax is 100 percent.

Sample No. 3 is the free base of (E)-N-methyl-4-[3-(5-isopropoxypyridin)yl]-3-buten-1-amine, and the manner of synthesis for that compound is set forth in U.S. Pat. No. 5,811,442 to Bencherif et al. The EC50 is 100 nM, and the Emax is 100 percent.

Sample No. 4 is the hemigalactarate salt of (E)-N-methyl-[3-(5-ethoxypyridin)yl]-3-buten-1-amine, and the manner of synthesis for that compound is set forth in U.S. Pat. No. 5,616,716 to Dull et al. The EC50 is less than 1 nM, and the Emax is 95 percent.

Sample No. 5 is the hemigalactarate salt of (E)-N-methyl-5-(3-pyridinyl)-4-penten-2-amine, and the manner of synthesis for that compound is set forth in U.S. Pat. No. 5,616,716 to Dull et al. The EC50 is less than 1 nM, and the Emax is 100 percent.

The EC50 is an indication of the concentration of compound that produced 50 percent maximal effect as determined by inhibition of decrease in metabolic rate. Emax values provide indication of inhibition of decrease of metabolic effect. A decrease in the metabolic activation of cells has been shown to reflect a decrease in cytokine release by those cells. The example provides indication that the compounds of the present invention have the capability to provide treatment of patients suffering from a condition resulting from dysfunction of cytokine production an/or release. The compounds of the present invention, in the therapeutic amounts used, do not cause any appreciable effects at muscle sites and ganglionic sites, thus indicating a lack of undesirable side effects by those compounds.

What is claimed is:

1. A pharmaceutical composition for inhibiting cytokine production and/or secretion, the pharmaceutical composition incorporating a compound having the formula:

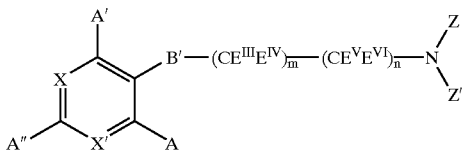

where X is nitrogen or carbon bonded to a substituent species, wherein the substituent species are selected from the group consisting of H, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", $CF_3$, OH, CN, $NO_2$, $C_2R'$, SH, $SCH_3$, $N_3$, $SO_2CH_3$, OR', $(CR'R")_qOR'$, O—$(CR'R")_qC_2R'$, SR', C(=O)NR'R", NR'C(=O)R", C(=O)R', (CR'R")$_qC_2R'$, C(=O)OR', OC(=O)R', OC(=O)NR'R" and NR'C(=O)OR', where q is an integer from 1 to 6 and R' and R" are individually hydrogen, alkyl, cycloalkyl, non-aromatic heterocyclic ring or an aromatic group-containing species; A, A' and A" are selected from the substituent species defined for X; B' is selected from:

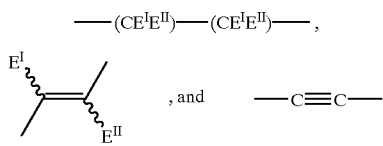

wherein X' is nitrogen; m is an integer and n is an integer such that the sum of m plus n is 1, 2, 3, 4, 5, 6, 7, or 8; $E^I$, $E^{II}$, $E^{III}$, $E^{IV}$, $E^V$ and $E^{VI}$ individually represent hydrogen, lower alkyl or halo substituted lower alkyl, such that at least one of $E^I$, $E^{II}$, $E^{III}$, $E^{IV}$, $E^V$ and $E^{VI}$ is not hydrogen; Z' and Z individually are hydrogen or lower alkyl; and the wavy-line in the structure indicates that the compound can have a cis (Z) or trans (E) form.

2. The pharmaceutical composition claim 1, wherein m plus n is 2 or 3.

3. The pharmaceutical composition claim 1, wherein A is hydrogen.

4. The pharmaceutical composition claim 1, wherein A, A' and A" are all hydrogen.

5. The pharmaceutical composition claim 1, wherein one or two of the substituents designated as $E^I$, $E^{II}$, $E^{III}$, $E^{IV}$, $E^V$ and $E^{VI}$ are non-hydrogen substituents.

6. The pharmaceutical composition claim 5, wherein $E^I$, $E^{II}$, $E^{III}$, $E^{IV}$, and $E^V$ are hydrogen and whereby $E^{VI}$ is non-hydrogen.

7. The pharmaceutical composition claim 5 wherein $E^I$ and $E^{II}$ are hydrogen.

8. The pharmaceutical composition claim 1 wherein B' is

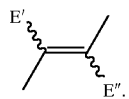

9. The pharmaceutical composition claim 1, wherein the compound has a trans (E) form.

10. The pharmaceutical composition claim 1, wherein at least one of Z' and Z are hydrogen.

11. The pharmaceutical composition claim 1, wherein Z is hydrogen and Z' is methyl.

12. A method of treating an autoimmune disorder, the method comprising administering an effective amount of the pharmaceutical composition claim 1 to a subject.

13. The pharmaceutical composition claim 1, wherein the compound is selected from the group consisting of (3E) and (3Z)-N-methyl-4-(3-pyridyl)-2-methyl-3-buten-1-amine, (3E) and (3Z)-N-methyl-4-(3-pyridyl)-3-methyl-3-buten-1-amine, (5E) and (5Z)-N-methyl-6-(3-pyridyl)-5-hexen-3-amine, (4E) and (4Z)-N-methyl-5-(3-pyridyl)-2-methyl-4-penten-2-amine, (4E) and (4Z)-N-methyl-5-(3-pyridyl)-3-methyl-4-penten-2-amine, (4E) and (4Z)-N-methyl-5-(3-pyridyl)-4-penten-2-amine, (4E) and (4Z)-N-methyl-5-(3-pyridyl)-1,1,1-trifluoro-4-penten-2-amine, (4E) and (4Z)-N-methyl-5-(3-pyridyl)-4-methyl-4-penten-1-amine, (4E) and (4Z)-N-methyl-5-3-pyridyl)-4-methyl-4-penten-2-amine, (1E) and (1Z)-N-methyl-1-(3-pyridyl)-1-octen-4-amine, (1E) and (1Z)-N-methyl-1-(3-pyridyl)-5-methyl-1-hepten-4-amine, (5E) and (5Z)-N-methyl-6-(3-pyridyl)-5-methyl-5-hexen-2-amine, (5E) and (5Z)-N-methyl-6-(3-pyridyl)-5-hexen-2-amine, (5E) and (5Z)-N-methyl-6-(3-pyridyl)-5-methyl-5-hexen-3-amine, (3E) and (3Z)-4-(3-pyridyl)-2-methyl-3-buten-1-amine, (3E) and (3Z)-4-(3-pyridyl)-3-methyl-3-buten-1-amine, (5E) and (5Z)-6-(3-pyridyl)-5-hexen-3-amine, (4E) and (4Z)-5-(3-pyridyl)-2-methyl-4-penten-2-amine, (4E) and (4Z)-5-(3-pyridyl)-3-methyl-4-penten-2-amine, (4E) and (4Z)-5-(3-pyridyl)-4-penten-2-amine, (4E) and (4Z)-5-(3-pyridyl)-1,1,1-trifluoro-4-penten-2-amine, (4E) and (4Z)-5-(3-pyridyl)-4-methyl-4-penten-1-amine, (4E) and (4Z)-5-(3-pyridyl)-4-methyl-4-penten-2-amine, (1E) and (1Z)-1-(3-pyridyl)-1-octen-4-amine, (5E) and (5Z)-6-(3-pyridyl)-5-methyl-5-hexen-2-amine, (5E) and (5Z)-6-(3-pyridyl)-5-hexen-2-amine, and (5E) and (5Z)-6-(3-pyridyl)-5-methyl-5-hexen-3-amine.

14. The pharmaceutical composition claim 1, wherein at least one of $E^{III}$, $E^{IV}$, $E^{V}$ and $E^{VI}$ is different from the remaining $E^{III}$, $E^{IV}$, $E^{V}$ and $E^{VI}$.

15. A pharmaceutical composition for inhibiting cytokine production and/or secretion, the pharmaceutical composition incorporating a compound having the formula:

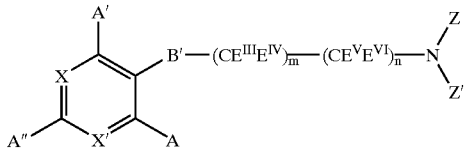

where X and X' individually are nitrogen or carbon bonded to a substituent species wherein the substituent species are selected from the group consisting of H, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", $CF_3$, OH, CN, $NO_2$, $C_2R'$, SH, $SCH_3$, $N_3$, $SO_2CH_3$, OR', $(CR'R")_qOR'$, O—$(CR'R")_qC_2R'$, SR', C(=O)NR'R", NR'C(=O)R", C(=O)R', $(CR'R")_qC_2R'$, C(=O)OR', OC(=O)R', OC(=O)NR'R" and NR'C(=O)OR', where q is an integer from 1 to 6 and R' and R" are individually hydrogen or lower alkyl; A, A' and A" are selected from the substituent species defined for X, and $NX^{III} X^{IV}$, wherein $X^{III}$ and $X^{IV}$ are individually hydrogen, alkyl cycloalkyl, non-aromatic heterocyclic ring or an aromatic group-containing species; B' is selected from the group consisting of consisting of oxygen, sulfur, a nitrogen containing moiety and

—CE'E"—X"— wherein X" is oxygen, nitrogen-containing moiety or sulfur; m is an integer and n is an integer such that the sum of m plus n is 1, 2, 3, 4, 5, 6, 7, or 8; $E^{I}$, $E^{II}$, $E^{III}$, $E^{IV}$, $E^{V}$ and $E^{VI}$ individually represent hydrogen, lower alkyl or halo substituted lower alkyl, such that at least one of $E^{I}$, $E^{II}$, $E^{III}$, $E^{IV}$, $E^{V}$ and $E^{VI}$ is not hydrogen; Z and Z' individually are hydrogen or lower alkyl; and the wavy-line in the structure indicates that the compound can have a cis (Z) or trans (E) form.

16. The pharmaceutical composition claim 15, wherein X' is nitrogen.

17. The pharmaceutical composition claim 15, wherein m plus n is 2 or 3.

18. The pharmaceutical composition claim 15, wherein A is hydrogen.

19. The pharmaceutical composition claim 15, wherein A, A' and A" are all hydrogen.

20. The pharmaceutical composition claim 15, wherein A, A', A" are independently selected from $NX^{III} X^{IV}$, wherein $X^{III}$ and $X^{IV}$ are individually hydrogen or lower alkyl.

21. The pharmaceutical composition claim 15, wherein one or two of the substituents designated as $E^{I}$, $E^{II}$, $E^{III}$, $E^{IV}$, $E^{V}$ and $E^{VI}$ are non-hydrogen substituents.

22. The pharmaceutical composition claim 21, wherein $E^{I}$, $E^{II}$, $E^{III}$, $E^{IV}$ and $E^{V}$ are hydrogen and whereby $E^{VI}$ is non-hydrogen.

23. The pharmaceutical composition claim 21, wherein $E^{I}$, and $E^{II}$ are hydrogen.

24. The pharmaceutical composition claim 15, wherein at least one $E^{III}$, $E^{IV}$, $E^{V}$ and $E^{VI}$ is different from the remaining $E^{III}$, $E^{IV}$, $E^{V}$ and $E^{VI}$.

25. The pharmaceutical composition claim 15, wherein the compound has a trans (E) form.

26. The pharmaceutical composition claim 15, wherein at least one of Z' and Z are hydrogen.

27. The pharmaceutical composition claim 15, wherein Z is hydrogen and Z' is methyl.

28. A method of treating an autoimmune disorder, the method comprising administering an effective amount of the pharmaceutical composition claim 15 to a subject.

29. A pharmaceutical composition comprising a compound selected from the group consisting of (3-(3-pyridyloxy)propyl)methylamine, (3-(3-pyridyloxy)propyl)amine, (3-(5-bromo-(3-pyridyloxy)propyl))methylamine, (1-methyl-3-(3-pyridyloxy)propyl)-methylamine, 3-(5-ethoxy-(3-pyridyloxy)propyl)methylamine, (3-(6-methyl-(3-pyridyloxy)propyl))methylamine, (3-(5-chloro-(3-pyridyloxy)propyl))methylamine, (3-(2-bromo(3-pyridyloxy)propyl))methylamine, (1-methyl-3-(5-methoxy-(3-pyridyloxy)propyl))methylamine, (4-(3-pyridyloxy)butyl)methylamine, (3-phenoxypropyl)methylamine, (3-(3-aminophenoxy)propyl)methylamine, and (3-(4-methoxyphenoxy)propyl)methylamine.

30. A pharmaceutical composition for inhibiting cytokine production and/or secretion, the pharmaceutical composition incorporating a compound having the formula:

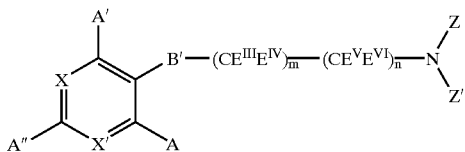

where X is nitrogen or carbon bonded to a substituent species and X' is carbon bonded to a substituent species wherein the substituent species are selected from the group consisting of H, alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl, F, Cl, Br, I, NR'R", $CF_3$, OH, CN, $NO_2$, $C_2R'$, SH, $SCH_3$, $N_3$, $SO_2CH_3$, OR', $(CR'R")_qOR'$, $O—(CR'R")_qC_2R'$, SR', C(=O)NR'R", NR'C(=O)R", C(=O)R', $(CR'R")_qC_2R'$, C(=O)OR', OC(=O)R', OC(=O)NR'R" and NR'C(=O) OR', where q is an integer from 1 to 6 and R' and R" are individually hydrogen or lower alkyl; A, A' and A" are selected from the substituent species defined for X and X', and $NX^{III}X^{IV}$, wherein $X^{III}$ and $X^{IV}$ are individually hydrogen or lower alkyl; B' is selected from the group consisting of oxygen, sulfur, a nitrogen containing moiety,

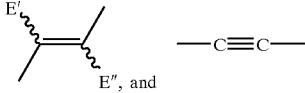

wherein X" is oxygen, nitrogen-containing moiety or sulfur; m is an integer and n is an integer such that the sum of m plus n is 1, 2, 3, 4, 5, 6, 7, or 8; $E^I$, $E^{II}$, $E^{III}$, $E^{IV}$, $E^V$ and $E^{VI}$ individually represent hydrogen, lower alkyl or halo substituted lower alkyl, such that at least one of $E^I$, $E^{II}$, $E^{III}$, $E^{IV}$, $E^V$ and $E^{VI}$ is not hydrogen; Z and Z' individually are hydrogen, alkyl cycloalkyl, non-armatic heterocyclic ring or an aromatic group-containing species; and the wavy-line in the structure indicates that the compound can have a cis (Z) or trans (E) form.

31. The pharmaceutical composition claim 30, wherein B' is oxygen.

32. The pharmaceutical composition claim 30, wherein m plus n is 2 or 3.

33. The pharmaceutical composition claim 30, wherein A is hydrogen.

34. The pharmaceutical composition claim 30, wherein A, A' and A" are all hydrogen.

35. The pharmaceutical composition claim 30, wherein A, A', A" are independently selected from $NX^{III}X^{IV}$, wherein $X^{III}$ and $X^{IV}$ are individually hydrogen or lower alkyl.

36. The pharmaceutical composition claim 30, wherein one or two of the substituents designated as $E^I$, $E^{II}$, $E^{III}$, $E^{IV}$, $E^V$ and $E^{VI}$ are non-hydrogen substituents.

37. The pharmaceutical composition claim 36, wherein $E^I$, $E^{II}$, $E^{III}$, $E^{IV}$ and $E^V$ are hydrogen and whereby $E^{VI}$ is non-hydrogen.

38. The pharmaceutical composition claim 36, wherein $E^I$ and $E^{II}$ are hydrogen.

39. The pharmaceutical composition claim 30, wherein at least one of $E^{III}$, $E^{IV}$, $E^V$ and $E^{VI}$ is different from the remaining $E^{III}$, $E^{IV}$, $E^V$ and $E^{VI}$.

40. The pharmaceutical composition claim 30, wherein the compound has a trans (E) form.

41. The pharmaceutical composition claim 30, wherein at least one of Z' and Z are hydrogen.

42. The pharmaceutical composition claim 30, wherein Z is hydrogen and Z' is methyl.

43. A method of treating an autoimmune disorder, the method comprising administering an effective amount of the pharmaceutical composition of claim 30 to a subject.

* * * * *